US006140087A

United States Patent [19]
Graham et al.

[11] Patent Number: 6,140,087
[45] Date of Patent: Oct. 31, 2000

[54] ADENOVIRUS VECTORS FOR GENE THERAPY

[75] Inventors: Frank L. Graham; Andrew Bett, both of Hamilton; Ludvik Prevec, Burlington; Wael M. Haddara, Kingston, all of Canada

[73] Assignee: AdVec, Inc., Hamilton, Canada

[21] Appl. No.: 08/250,885

[22] Filed: May 31, 1994

Related U.S. Application Data

[63] Continuation-in-part of application No. 08/080,727, Jun. 24, 1993, abandoned.
[51] Int. Cl.⁷ .......................... C12N 15/63; C12N 15/64; C12N 15/861; C07H 21/04
[52] U.S. Cl. ...................... 435/91.42; 435/320.1; 435/455; 435/456; 435/91.4; 536/23.72; 536/24.1
[58] Field of Search .......................... 514/44; 435/320.1, 435/455, 456, 91.4, 91.42; 424/93.21; 536/23.72, 24.1

[56] References Cited

U.S. PATENT DOCUMENTS

| | | | |
|---|---|---|---|
| 4,510,245 | 4/1985 | Cousens et al. | 435/69.3 |
| 4,797,368 | 1/1989 | Carter et al. | 435/320.1 |
| 4,920,209 | 4/1990 | Davis et al. | 435/235.1 |
| 4,920,211 | 4/1990 | Tibbetts et al. | 435/320.1 |
| 5,882,877 | 3/1999 | Gregory et al. | 435/320.1 |

FOREIGN PATENT DOCUMENTS

| | | |
|---|---|---|
| WO 93/06223 | 4/1993 | WIPO . |
| WO 93/19092 | 9/1993 | WIPO . |
| WO 93/19191 | 9/1993 | WIPO . |
| WO 94/08026 | 4/1994 | WIPO . |
| WO 94/12649 | 6/1994 | WIPO . |

OTHER PUBLICATIONS

Graham et al, Methods in Molecular Biology, 7:109–128 (1991).
Quantin et al., PNAS, vol. 89, pp. 2581–2584, Apr. 1992.
Yang et al., Proc. Natl. Acad. Sci. USA, 91:4407–4411 (1994).
Wolff, JA, Current Opinion in Neurobiology, 3:743–748 (1993).
Neuwalt et al., Behaviorial and Brain Sciences, 18:1–9 (1995).
B. Quantin, et al., "Adenovirus as an Expression Vector in Muscle Cells In Vivo", *Proc. Natl. Acad. Sci. USA*, vol. 89, 1992, pp. 2581–2584.
M. Rosenfeld, et al., "In Vivo Transfer of the Human Cystic Fibrosis Transmembrane Conductance Regulator Gene to the Airway Epitehlium", *Cell*, vol. 68, 1992, pp. 143–155.
W.J. McGrory et al., "A Simple Technique for the Rescue of Early Region I Mutations into Infectious Human Adenovirus Type", *Virology* 163, 1988, pp. 614–617.
G. Ghoush–Choudhury et al., "Human Adenovirus Cloning Vectors Based on Infectious Bacterial Plasmids", *Gene* 50, 1966, pp. 161–171.

Tomas Hanke et al., "Identification of an Immunodominant Cytooxic T–Lymphocyte Recognition Site in Glycoprotein B of Herpes Simplex Virus by Using Recombinant Adenovirus Vectors and Synthetic Peptides", *Journal of Virology*, 65 (3), 1991, pp. 1177–1186.

S.K. Mittal et al. (1993) *Virus Res.* 28, 67–90.

K.L. Berkner et al., "Generation of Adenovirus by Transfection of Plasmids", *Nucleic Acids Research*, 11(17), 1983, pp. 6003–6020.

Y. Haj–Ahmad et al., "Development of a Helper–Independent Human Adenovirus Vector and its Use in the Transfer of the Herpes Simplex Virus Thymidine Kinase Gene", *Journal of Virology*, 57(1), 1986, pp. 267–274.

N. Jones and T. Shenk, "Isolation of Adenovirus Type 5 Host Range Deletion Mutants Defective for Transformation of Rat Embryo Cells", *Cell*, 17, 1979, pp. 683–689.

D.S. Bautista et al., "Isolation and Characterization of Insertion Mutants in E1A of Adenovirus Type 5", *Virology*, 182, 1991, pp. 578–596.

F.L. Graham, "Covalently Closed Circles of Human Adenovirus DNA are Infectious", *The EMBO Journal*, 3(12), 1984, pp. 2917–2922.

M. Ruben et al. "Covaltently Closed Circles of Adenovirus 5 DNA" (1983) *Nature* 301: 172–174.

P. Hearing et al., "Identification of a Repeated Sequence Element Required to Efficient Encapsidation of the Adenovirus Type 5 Chromosome", *Journal of Virology*, 61(8), 1987, pp. 2555–2558.

N.D. Stow, "The Infectivity of Adenovirus Genomes Lacking DNA Sequences from their Left–hand Termini", *Nucleic Acids Research*, 10(17), 1982, pp. 5105–5119.

*Primary Examiner*—David Guzo
*Attorney, Agent, or Firm*—Gerald H. Bencen, Esq.; Timothy H. Van Dyke, Esq.; Bencen & Van Dyke, P.A.

[57] ABSTRACT

The invention comprises a series of adenovirus-based vectors having deletions in the E1 and/or E3 regions, and also insertions of pBR322 sequences, which can be used to deliver nucleic acid inserts into host cells, tissues or organisms that then can express the insert. The invention includes the use of the vectors in introducing genes into cells, in making vaccines and in gene therapy.

27 Claims, 16 Drawing Sheets

COTRANSFECTION OF 293 CELLS
INTRACELLULAR RECOMBINATION

INFECTIOUS VIRAL VECTOR

Protein IX →

ADENOVIRUS VECTORS FOR GENE THERAPY

This application is a continuation-in-part of application Ser. No. 08/080,727 filed Jun. 24, 1993, now abandoned, which is hereby incorporated by reference.

FIELD OF THE INVENTION

This invention relates to adenovirus (Ad) vectors that are useful for enhanced expression of selected nucleic acids in infected, transfected or transformed cells, especially eukaryotic mammalian cells. The vectors of the invention are also useful in the production of genetically engineered vaccines and for gene therapy.

BACKGROUND

Adenoviruses (Ads) are a relatively well characterized, homogeneous group of viruses. Roughly 100 different adenoviruses, including nearly 50 serotypes isolated from humans, have been identified to date.

Most common serotypes of Ads are nonpathogenic, physically and genetically stable, can be grown to very high titres (concentrated stocks with $10^{11}$–$10^{12}$ PFU/ml of infectious virus are easy to obtain) and easily purified by isopycnic centrifugation in CsCl gradients. The Ad genome is readily manipulated by recombinant DNA techniques, and the proteins encoded by foreign DNA inserts that are expressed in mammalian cells will usually be appropriately glycosylated or phosphorylated, unlike recombinant proteins expressed in bacteria, yeast, and some insect cells. Although human Ads replicate most efficiently in human cells of epithelial origin, these viruses infect almost any mammalian cell and express at least some viral genes. Unlike retroviruses, Ads will infect, and are expressed in, nonreplicating cells. Thus, Ad-based vectors may be useful for gene delivery, expression, and gene therapy.

Ad vectors have been constructed by ligation or recombination of viral DNA with subgenomic viral sequences contained in bacterial plasmids. Berkner, K. L. & Sharp, P. A. (1983) *Nucleic Acids Res.* 11: 6003–6020; Haj-Ahmad, Y & Graham, F. L. (1986) *J. Virol.* 57: 267–274; Stow, N. D. (1981) *J. Virol.* 37: 171–180. This approach has several drawbacks, which include the time and technical difficultly required to produce viral DNA, the background of infectious parental virus which makes screening more labor intensive and, in the case of direct ligation, the limited availability of useful restriction sites due to the relatively large size of the adenovirus genome.

Another strategy has been to recombine two plasmids which together contain sequences comprising the entire Ad genome. A number of conditionally defective plasmid systems have been developed making the construction of vectors simpler and reducing the number of subsequent analyses required to identify recombinant viruses. McGrory, W. J., Bautista, D. S. & Graham, F. L. (1983) *Virology* 163: 614–617; Ghosh-Choudhury, G., Haj-Ahmad, Y., Brinkley, P., Rudy, J. & Graham, F. L. (1986) *Gene* 50: 161–171; Mittal, S. K., McDermott, M. R. Johnson, D. C., Prevec, L. & Graham, F. L. (1993) *Virus Res.* 28, 67–90.

The representative Adenovirus 5 ("Ad5") genome used in embodiments of the present invention is a 36 kb linear duplex. Its sequence has been published. (Chroboczek, J., Bieber, F., and Jacrot, B. (1992) The Sequence of the Genome of Adenovirus Type 5 and Its Comparison with the Genome of Adenovirus Type 2, *Virology* 186, 280–285; hereby incorporated by reference). The Ad5 genome contains a 100–150 base pair (bp) inverted terminal repeat ("ITR") at each end of the linearized genome. A terminal protein ("TP") of 55,000 daltons is covalently linked to the 5' end of each strand. Both the TP and the ITRs are thought to play a role in viral DNA replication. McGrory, W. J. et al. (1988), *Virology,* 163, 614–617 and Ghosh-Choudhury, G. et al. (1986), *Gene,* 50, 161–171 (hereby incorporated by reference). Ad5 has infected each human cell line tested, although some cells, such as lymphocytes, are relatively nonpermissive.

Four noncontiguous regions of the Ad5 genome are transcribed early in infection, prior to DNA replication. These regions are early region 1 (E1) (about 1.3–11.2 mu of or about position 198–4025 bp of a standardized genome, inclusive of the E1A enhancer region; Sussenbach, J. S., in Ginsburg (Ed.), *The Adenoviruses* pp. 35–124, 1984, Plenum Press) which is further divided into subregions E1A and E1B; early region 2 (E2), which encodes the DNA replicative functions of the virus; early region 3 (E3) (about 75.9–86.0 mU, or about 27,275–30,904 bp; Cladaras, C. and Wold, W. S. M. (1985) *Virol.* 140, 28–43; and early region 4 (E4). E1A is involved in turning on the other early regions and in regulating a number of host cell functions. E1B and E4 are primarily involved in shutting off the host cell's protein synthesis. E3 regulates the host cell's immune response to virus infection. Some of these early genes function to "turn on" later-expressed genes that are needed to replicate the genome and form viable viral particles.

The Ad virion has the ability to package up to 105–106% of the wild type genome length. Bett, A. J., Prevec, L., & Graham, F. L. (1993) Packaging Capacity and Stability of Human Adenovirus Type 5 Vectors, *J. Virol.* 67: 5911–5921. Larger genomes (e.g., 108% of the wild type in size), result in instability of the virus and poor growth rates. Id. This packaging ability allows the insertion of only approximately 1.8–2.0 kb of excess DNA into the Ad genome.

To package larger inserts, it is necessary to first delete portions of the viral genome. Parts of region E1 can be deleted, and the resulting viruses can be propagated in human 293 cells. (293 cells contain and express E1, complementing viral mutants that are defective in E1.) Foreign nucleic acids can be inserted in place of E1, in Ad5 genomes that contain E1 deletions of up to 2.9 kb, to yield conditional helper-independent vectors with a capacity for inserts of 4.7–4.9 kb.

Viruses with a region E3 deletion can also replicate in cultured human cells such as HeLa or KB and infect and be expressed in animals including humans. A deletion of a 3.0 kb E3 sequence has been reported, without a concomitant insertion. Ranheim, T. S., Shisler, J., Horton, T. M., Wold, L. J. Gooding, L. R., and Wold, W. S. M. (1993) *J. Virol.* 67, 2159–2167.

Among the methods developed to date there is no simple procedure for generating vectors that utilize both E1 and E3 deletions. In addition, the vectors that do utilize either E1 or E3 deletions can accomodate only relatively small inserts. To simplify the production and use of Ad vectors that can tolerate larger fragments, we have developed a new methodology based on a series of bacterial plasmids that contain most of an Ad viral genome.

SUMMARY OF THE INVENTION

It is a goal of this invention to provide simple, flexible, efficient, high capacity Ad 5 cloning and expression vectors. Accordingly, a new vector system Las been developed which comprises expanded deletions in both E1 and E3 and further combines them in a single vector system that can tolerate inserts of up to 8000 bp, enough to accommodate the majority of protein coding genes along with control elements to regulate expression. The invention provides the option of cloning foreign nucleic acids into either or both of the E1 or E3 regions and promises to be the most versatile and easy to use technology yet developed. In addition, a modification of the system permits construction of viruses carrying a wild type E3 region, and insertions, substitutions, or mutations in the E1 region.

One embodiment of the present invention provides a bacterial plasmid comprising a circularized modified human adenovirus type 5 (Ad5) genome. The nucleotide sequence of the plasmid has a deletion within early region 3 (E3) of said Ad5 genome, and a segment of bacterially replicable pBR322 plasmid encoding ampicillin resistance substituted for a sequence of early region 1A (E1A) that corresponds, in whole or in part, to the packaging signal.

Another embodiment provides a bacterial plasmid comprising approximately 340 base pairs from the left end of the adenovirus type 5 genome, the left end inverted terminal repeat sequences of said genome and the packaging signal sequences thereof, said plasmid comprising also a eukaryotic gene sequence of up to about 8 kilobases foreign to said plasmid and to said viral genome. The adenovirus sequence from approximately nucleotide position 3540 thereof to approximately position 5790 thereof is present on the right side of said foreign sequence.

Other embodiments of the present invention include adenovirus genome constructs containing E1 deletions and foreign inserts of eukaryotic origin, using any combination of size of E1 deletion and/or of size of foreign insert that can be accommodated in the plasmid and still remain operable. Because of the large capacity of the vectors provided herein, multiple inserts of foreign genes can be placed in the E1 cloning site. For example, two or more genes encoding different antigens, or genes encoding useful proteins, can be combined with genes encoding chemically selectable markers.

One specific embodiment of the invention, the plasmid pBHG10, may be used to insert foreign genes into either the E3 or E1 region of the Ad5 genome. Genes inserted into E3 can be combined with a variety of mutations, deletions, or insertions in E1 by appropriate choice of the cotransfected plasmid containing left end (E1) sequences.

The vectors provided herein can be used in gene transfer or in gene therapy to treat a variety of genetic defects and pathological conditions.

BRIEF DESCRIPTION OF THE DRAWINGS

FIG. 1 is a diagrammatic representation of the structure and construction of the vector pBHG10.

FIG. 2 is a diagrammatic representation of the structure and construction of the vector pBHG3.

FIG. 8 depicts the strategy for the construction of a double recombinant containing lacZ in the E3 deletion and firefly luciferase in the E1 deletion.

DETAILED DESCRIPTION OF THE INVENTION

Figure 1A:
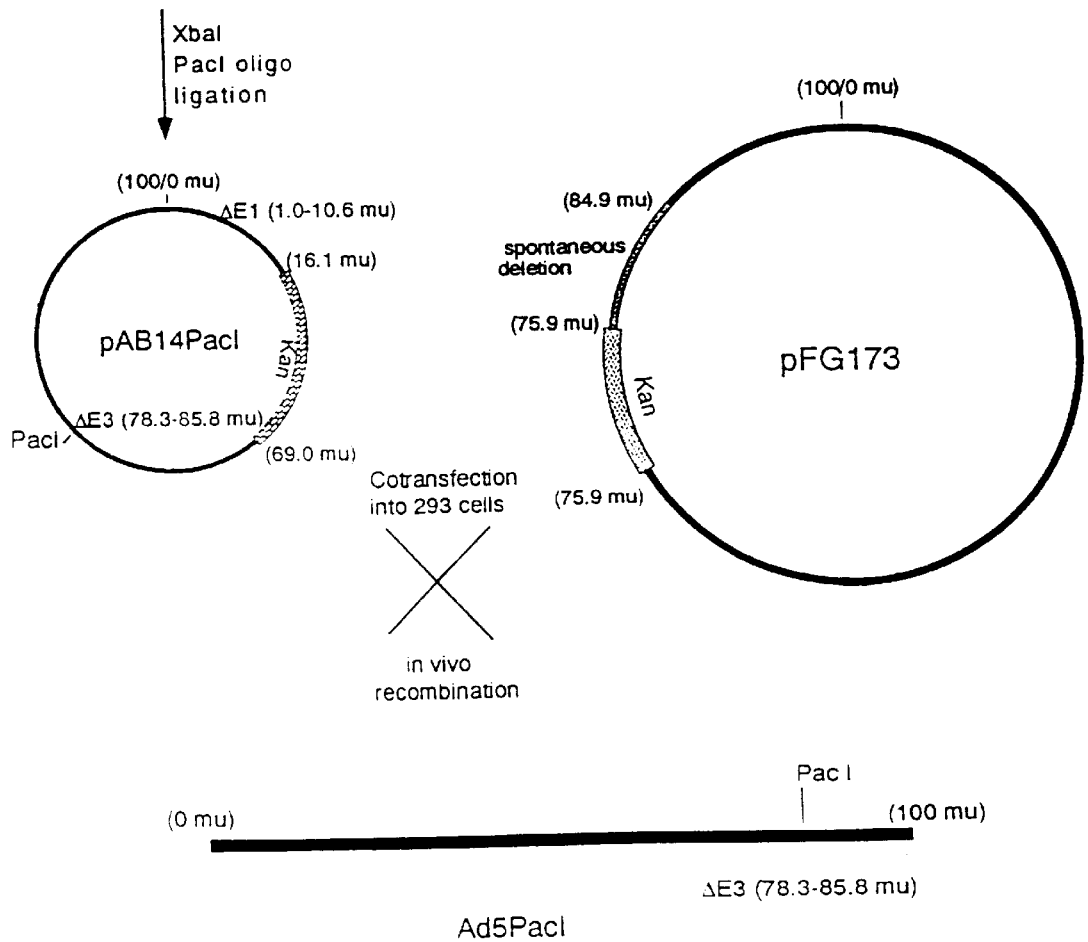
FIG. 1A is a diagrammatic representation of the structure and construction of nucleic acid encoding Ad5PacI.

The recombinant Ad vectors provided herein are significantly different from previously reported constructs because they contain the largest possible deletion of E1 sequences (within 30–40 bp) that can be made while still allowing the generation of viable viral recombinants. Surprisingly, the different genetic elements described herein, when combined, produced a stable construct useful in introducing and expressing foreign nucleic acids in host cells.

At the onset of these experiments, it was unknown how large a deletion could be, or where it could be placed, without affecting the growth, production and infectivity of packaged virions. For viral viability and maximum packaging capacity, deletions in the E1 region preferably should not affect the left inverted terminal repeat (ITR; 1–103 bp) or packaging signals (194–358 bp). Hearing, P. and Shenk, T., (1983) Cell 33, 695–703; Grable, M. and Hearing, P. (1992) J. Virol. 64, 2047–2056. In addition, because the only currently available E1 complementing cell line (293 cells) does not express protein IX, deletions should not extend into the coding sequences for this polypeptide. (Although viral deletion mutants lacking the protein IX gene have been isolated, it appears that the protein is essential for packaging of full length genomes into functional virus.)

In the pBHG plasmid embodiments of the invention, the pBR322 sequences substitute for Ad5 sequences from position 188 to 1339, which include the packaging signal, E1A enhancer, promoter and most of the E1A protein coding sequences. The pBR322 insert not only contains an ampicillin resistance, but allows the pBHG family of vectors to be replicated in cells wherein pBR322 may be replicated.

Some embodiments of the invention herein contain a deletion of the E1 region between an Ssp I site at 339 bp and an Afl site at 3533 bp which results in removal of the SP1 binding site (3525–3530 bp). Since the Sp1 site may be essential for protein IX expression, it was reintroduced as a synthetic oligonucleotide which positioned the Sp1 site closer to the protein IX TATA box than is the case in the wild type (wt) protein IX gene.

Definitions

It is important to a clear understanding of the present invention to understand that a number of the terms used herein are not intended to be limiting, even though common usage might suggest otherwise. For example, the term "nucleic acid" is used interchangeably with gene, cDNAs, RNA, or other oligonucleotides that encode gene products.

"Vector" denotes a genetically engineered nucleic acid construct capable of being modified by genetic recombinant techniques to incorporate any desired foreign nucleic acid sequence, which may be used as a means to introduce said sequence in a host cell, replicate it, clone it, and/or express said nucleic acid sequence, wherein said vector comprises all the necessary sequence information to enable the vector to be replicated in host cells, and/or to enable the nucleic acid sequence to be expressed, and/or to enable recombination to take place, and/or to enable the vector to be packaged in viral particles. This recitation of the properties of a vector is not meant to be exhaustive.

"Modification" of a nucleic acid includes all molecular alterations of a nucleic acid sequence that change its capacity to perform a stated function, specifically including deletions, insertions, chemical modifications, and the like. Insertions and deletions may be made in a number of ways known to those skilled in the art, including enzymatically cutting the full length sequence followed by modification and ligation of defined fragments, or by site-directed mutagenesis, especially by loop-out mutagenesis of the kind described by Kramer et al. (1984), Nucl. Acids Res. 12: 9441–9456.

"Fragment" or "subfragment" refers to an isolated nucleic acid derived from a reference sequence by excising or deleting one or more nucleotides at any position of the reference sequence using known recombinant techniques, or by inserting a predetermined sequence of nucleotides at any predetermined position within the reference sequence using known recombinant techniques.

"Expression of" or "expressing" a foreign nucleic acid, gene or cDNA is used hereinafter to encompass the replication of a nucleic acid, the transcription of DNA and/or the translation of RNA into protein, in cells or in cell-free systems such as wheat germ or rabbit reticulocytes. The term "foreign" indicates that the nucleic acid is not found in nature identically associated with the same vector or host cell, but rather that the precise association between the said nucleic acid and the vector or host cell is created by genetic engineering. It is not intended that the invention be limited to the use of nucleic acid sequences from any particular species or genus, but that this invention can be carried out using nucleic acids from a variety of sources. It is contemplated that any nucleic acid from any source may be inserted into the vector, with or without control elements.

Vectors, optionally containing a foreign nucleic acid, may be "introduced" into a host cell, tissue or organism in accordance with known techniques, such as transformation, transfection using calcium phosphate-precipitated DNA, electroporation, gene guns, transfection with a recombinant virus or phagemid, infection with an infective viral particle, injection into tissues or microinjection of the DNA into cells or the like. Both prokaryotic and eukaryotic hosts may be employed, which may include bacteria, yeast, plants and animals, including human cells.

Once a given structural gene, cDNA or open reading frame has been introduced into the appropriate host, the host may be grown to express said structural gene, cDNA or open reading frame. Where the promoter is inducible, permissive conditions may be employed (for example, temperature change, exhaustion, or excess of a metabolic product or nutrient, or the like).

The expression vehicles used or provided herein may be included within a replication system for episomal maintenance in an appropriate cellular host, they may be provided without a replication system, or they may become integrated into the host genome.

While a wide variety of host cells are contemplated, certain embodiments require that the host cell express E1 sequences that are missing from or inactivated in the vector. While the human 293 cell line is the preferred host cell, the invention also contemplates other cell lines capable of complementing the vector having an E1 deletion. It is important to recognize that the present invention is not limited to the use of such cells as are used herein. Cells from different species (human, mouse, etc.) or different tissues (breast epithelium, colon, neuronal tissue, lymphocytes, etc.) may also be used.

"Complementing" or "complemented by" denotes that the host cell line encodes and/or expresses functions that are necessary for generating viable viral particles that are missing from or have been inactivated in the vector.

"Gene therapy" comprises the correction of genetic defects as well as the delivery and expression of selected nucleic acids in a short term treatment of a disease or pathological condition.

It is important to an understanding of the present invention to note that all technical and scientific terms used herein, unless otherwise defined, are intended to have the same meaning as commonly understood by one of ordinary skill in the art; that techniques employed herein are also those that are known to one of ordinary skill in the art, unless stated otherwise; and that publications mentioned herein are incorporated by reference.

It is also important to note that reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, etc., such that a different but known way is used to achieve the same goals as those to which the use of a suggested method, material or composition is directed.

It is also important to note that the present invention is not limited to the use of all of the described discoveries or embodiments explicitly described herein. Although combining them may indeed be preferred, it is not necessary to the invention that all aspects be used simultaneously.

Where the exogenous nucleic acid is to be expressed in a host which does not recognize the nucleic acid's naturally occurring transcriptional and translational regulatory regions, a variety of transcriptional regulatory regions may be inserted upstream or downstream from the coding region, some of which are externally inducible. Illustrative transcriptional regulatory regions or promoters for use in bacteria include the β-gal promoter, lambda left and right promoters, trp and lac promoters, trp-lac fusion promoter, and also the bacteriophage lambda $P_L$ promoter together with the bacteriophage lambda $O_L$ operator and the CI857 temperature-sensitive repressor, for example, to provide for temperature sensitive expression of a structural gene. Regulation of the promoter is achieved through interaction between the repressor and the operator. For use in yeast, illustrative transcriptional regulatory regions or promoters include glycolytic enzyme promoters, such as ADH-I and -II promoters, GPK promoter, and PGI promoter, TRP promoter, etc.; for use in mammalian cells, transcriptional control elements include SV40 early and late promoters, adenovirus major late promoters, etc. Other regulatory sequences useful in eucaryotic cells can include, for example, the cytomegalovirus enhancer sequence, which can be fused to a promoter sequence such as the SV40 promoter to form a chimeric promoter, or can be inserted elsewhere in the expression vehicle, preferably in close proximity to the promoter sequence.

When desired, expression of structural genes can be amplified by, for example, ligating in tandem a nucleic acid for a dominant amplifiable genetic marker 5' or 3' to the structural gene and growing the host cells under selective conditions. An example of an amplifiable nucleic acid is the gene for dihydrofolate reductase, expression of which may be increased in cells rendered resistant to methotrexate, a folate antagonist.

Recombinant DNA constructs prepared for the purposes of this invention may be introduced into the host in accordance with known techniques, such as transformation, transfection using calcium phosphate-precipitated DNA, electroporation, transfection with a recombinant virus, microinjection of the DNA into cells or the like.

The isolated nucleic acids of this invention can be used to generate modified polypeptides, each having at least one characteristic of the native polypeptide. These include subfragments, deletion mutants, processing mutants, or substitution mutants, polypeptides having the same secondary structure as the binding region of the native polypeptide, and combinations thereof. Such modified polypeptides may carry the functionality of the "wild type" peptide, or may have a modified or externally regulatable functionality. Such modified polypeptides may have considerable utility in the present invention, as would be appreciated by those skilled in the art.

"Wild type", mutant and analogous polypeptides and compositions thereof may be used for making antibodies, which may find use in analyzing results of the assays described as part of this invention. The antibodies may be prepared in conventional ways, either by using the subject polypeptide as an immunogen and injecting the polypeptide into a mammalian host, e.g., mouse, cow, goat, sheep, rabbit, etc., particularly with an adjuvant, e.g., complete Freund's adjuvant, aluminum hydroxide gel, or the like. The host may then be bled and the blood employed for isolation of polyclonal antibodies, or the peripheral blood lymphocytes (B-cells) may be fused with an appropriate myeloma cell to produce an immortalized cell line that secretes monoclonal antibodies specific for the subject compounds.

The following examples and instructions are not intended in any way to be limiting, as it should be readily apparent to those skilled in the art how alternative means might be used to achieve the results that this invention provides.

The following experimental methods, having been used by us to demonstrate and illustrate the present invention, are described in substantial detail hereinbelow. However, these details are not intended to be limiting, and those skilled in the art will appreciate that many other methods could be used to verify and explore the screening methods and cell lines that comprise the present invention.

Materials and Methods

Enzymes used for recombinant DNA manipulations were purchased from Boehringer-Mannheim, Inc. (Laval, Quebec, Canada), New England Biolabs (Beverly, Mass.) or Bethesda Research Laboratories (Burlington, Ontario, Canada) and used according to the supplier's recommendations. Plasmids were constructed using standard protocols. Sambrook, J., E. F. Fritsch, and T. Maniatis. 1989. Molecular Cloning: A Laboratory Manual. 2nd Ed. Cold Spring Harbor Laboratory, Cold Spring Harbor, N.Y. Electroporation was used to transform E. coli strain DH5 (supE44 hsdR17 recA1 endA1 gyrA96 thi-1 relA1) with newly constructed plasmids. Dower, W. J., J. F. Miller, and C. W. Ragsdale. 1988. High efficiency transformation of E. coli by high voltage electroporation. Nucleic Acids Res. 16: 6127–6145. Plasmid DNA was prepared by the alkaline lysis method and purified by CsCl-Ethidium Bromide density gradient centrifugation. Birnboim, H. C., and J. Doly. 1978. A rapid alkaline extraction procedure for screening recombinant plasmid DNA. Nucleic Acids Res. 7:1513–1523.

Cells and Viruses

Cell culture media and reagents were obtained from GIBCO Laboratories (Grand Island, N.Y.). Adenovirus (Ad) vectors were tittered and passaged on 293 cells which constitutively express the left 11% of the Ad5 genome, comprising the E1 region. Graham, F. L., J. Smiley, W. C. Russell, and R. Nairn. 1977. Characteristics of a human cell line transformed by DNA from human adenovirus type 5. J. Gen. Virol. 36:59–72. The 293 cells were grown in monolayer in F-11 minimum essential medium supplemented with 100 units penicillin/ml, 100 µg streptomycin/ml, 2.5 µg amphotericin/ml and with 10% newborn calf serum for cell maintenance or 5% horse serum for virus infection. KB cells grown in spinner culture were maintained in Joklik's modified medium supplemented with antibiotics as above and with 10% horse serum.

For one step growth curves KB cells were grown to a density of $2\times10^5$ cells/ml, centrifuged, and resuspended in 1/10th the volume of original medium and virus was added (20 PFU/cell) and allowed to adsorb for 1 h at 37° C. with shaking. The cells were then returned to the original volume using 50% fresh and 50% original medium. At various times post-infection 4 ml aliquots were taken, 0.5 ml of glycerol added, and the samples were stored at −70° C. for assays of infectious virus by plaque titration.

Construction and Growth of Recombinant Viruses

Recombinant viruses were isolated by cotransfection of 293 cells with appropriate plasmids. Graham, F. L., and A. J. Van der Eb. 1973. A new technique for the assay of infectivity of human adenovirus 5 DNA. Virology 52:456–467. After 8–10 days plaques were isolated, expanded and viral DNA analyzed by restriction enzyme digestion as described previously. Graham, F. L. and L. Prevec. 1991. Manipulation of Adenovirus Vectors, p. 109–128. In E. J. Murry (ed.) Methods in Molecular Biology, Vol. 7: Gene Transfer and Expression Protocols. The Humana Press Inc., Clifton, N.J. Candidate viruses were then plaque purified once and, for stability studies, vectors were passaged starting with medium from cells infected for viral DNA analysis after the first plaque purification. Semiconfluent monolayers of 293 cells in 60 mm dishes were infected with 0.5 ml of medium from each previous passage (approximately 40 PFU/cell), virus was allowed to adsorb for one half hour and then medium was replaced. Cells and medium were harvested when cytopathic effect was complete, usually within 2–3 days postinfection.

$^{32}$P Labelling and Extraction of Viral DNA

Semiconfluent monolayers of 293 cells in 60 mm dishes were infected with virus from passages to be analyzed and at 24 h postinfection, medium was removed and replaced with 1 ml of phosphate-free 199 medium containing 5% horse serum and 25 uCi/ml of $^{32}$P-orthophosphoric acid (purchased from DuPont de Nemours & Co., Inc., Wilmington, Del.). After incubating the infected cells for a further 6 h, the cells were harvested and DNA was extracted. Viral DNA was then digested with appropriate restriction enzymes, electrophoresed through 1% agarose gels and the gels were dried and DNA bands visualized by autoradiography.

Example 1

Generation of the Plasmid pBHG10

Adenoviruses carry a cis-acting sequence in the E1 region which is essential for encapsidation of viral DNA molecules. When this cis-acting signal, located from 194 to 358 bp in Ad5, is deleted, viral genomes cannot be packaged but would still be expected to replicate their DNA in transfected cells. This, the fact that Ad DNA can circularize in infected cells, and that the cotransfection into mammalian cells of two plasmids with overlapping sequences can generate infectious virus with good efficiency, led us to conceive the strategy described below.

The first step involved the construction of Ad5PacI, a virus which contains the entire Ad5 genome with a deletion of E3 sequences from 28133 to 30818 bp. Ad5PacI was made by cotransfection of 293 cells with two plasmids: pFG173; and pAB14PacI, a modified pAB14 (Bett, A. J., L. Prevec, and Graham, F. L. (1993) *J. Virol.* 67, 5911–5921) in which a PacI cloning site is substituted in place of 2.69 kb of E3. (FIG. 1A). Next, purified viral DNA from Ad5PacI was digested with ClaI and XbaI and was cotransfected into 293 cells with another plasmid, pWH3 (Bautista, D. S., and Graham, F. L. (1989) *Gene* 82, 201–208), to yield the virus AdBHG (FIG. 1B). pWH3 is a plasmid containing left end Ad5 sequences, with an insertion of modified pBR322 plasmid at bp 1339, designed so that the packaging signals could be deleted at a later stage.

The next step involved the generation of a bacterial plasmid containing the entire AdBHG genome and subsequent identification of infectious clones. Baby rat kidney (BRK) cells were infected with AdBHG under conditions previously shown to result in the generation of circular Ad5 genomes. Graham F. L. (1984) *EMBO J.* 3: 2917–2922; Ruben, M., Bacchetti, S. & Graham, F. L. (1983) *Nature* 301: 172–174. At 48 hours post-infection, DNA was extracted from the infected BRK cells and used to transform *E. coli* strain HMS 174 to ampicillin (Ap$^r$) and tetracycline resistance (Tet$^r$). From two experiments a total of 104 colonies were obtained.

Small scale plasmid preparations were screened by HindII and BamHI/SmaI digestion and gel electrophoresis. The results of the restriction analysis revealed that the plasmids varied in the amount of the viral genome which they contained. This is believed to be due, at least in part, to the formation of a 206 bp palindrome when the inverted terminal repeats (ITR's) of the Ad5 genome are joined head to tail (the junction).

From the restriction analysis four candidate plasmids were selected that appeared to posses a complete AdBHG genome with intact junction regions. All four plasmids were found to be infectious in infectivity assays in which 293 cells were transfected with 5 or 10 μg of plasmid DNA (data not shown).

The ITR junctions in each of the infectious clones were sequenced and analyzed. The number of nucleotides missing from the mid point of the palindrome in each clone varied from as few as 4 bp (1 bp from the right ITR and 3 bp from the left) to as many as 19 bp (1 bp from the right ITR and 18 bp from the left). For further work we chose the clone missing 19 bp from the junction and called this pBHG9.

Figure 1B:
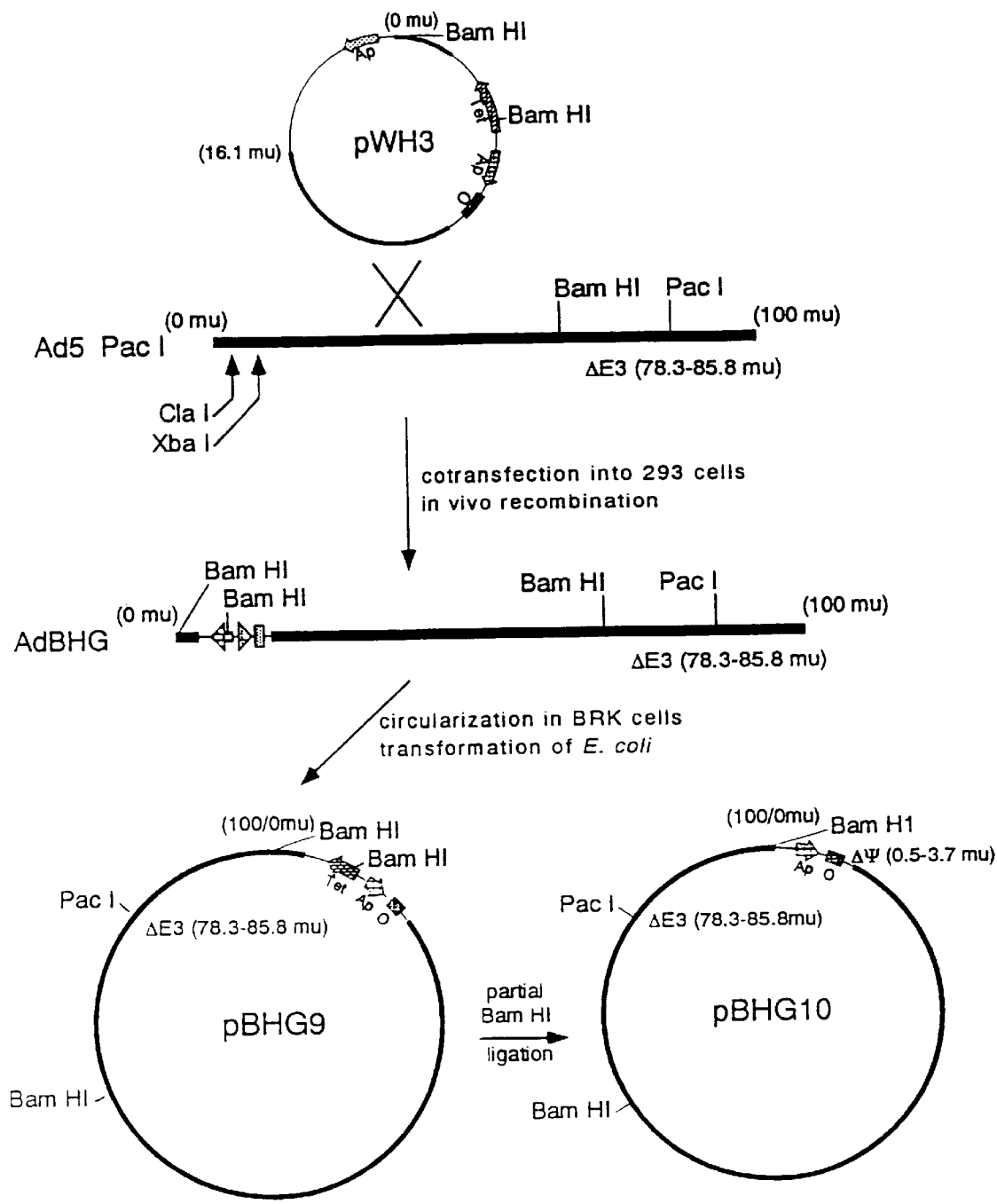
FIG. 1B is a diagrammatic representation of the structure and construction of the vectors pBHG9 and pBHG10.

PBHG10 was generated by deleting the packaging signals in pBHG9. This was accomplished by partial BamHI digestion and religation (FIG. 1B). Screening for pBHG10 was facilitated by the fact that removal of the packaging signals also resulted in the elimination of the Tet$^r$ gene.

pBHG10 contains Ad5 DNA sequences from bp 19 (left genomic end) to bp 188; bp 1339 to 28133; and bp 30818 to 35934 (right genomic end). The left and right termini of the Ad5 genomes are covalently joined. A segment of plasmid pBR322, representing nucleotides 375-1/4361-2064 of the pBR322 genome, which includes the pBR322 origin of replication and the pBR322 ampicillin resistance gene, is present between Ad5 bp 188 and 1339 to allow propagation of pBHG10 in host cells such as *E. coli*. A PacI restriction enzyme site, unique in this plasmid, is present between Ad5 bp 28133 and bp 30818 to permit insertion of foreign genes.

Because the packaging signal is deleted, pBHG10 by itself does not yield infectious viral particles. Cotransfections of pBHG10 with helper plasmids containing the left end of Ad5 sequences, including the packaging signal, yields through recombination in the host cell infectious viral vectors with an efficiency comparable to that obtained using pJM17.[1]

[1] Although pJM17 has been found useful for rescue of E1 mutations or substitutions into infectious virus, it has neither a wild type E3 region nor a useful E3 deletion. McGrory, W. J., Bautista, D. S. & Graham, F. L. (1988) *Virology* 163, 614–617 (unpublished and see below). Thus, pJM17 will be superseded by the pBHG series of plasmids for most Ad5 vector constructions.

Example 2

Figure 2A:
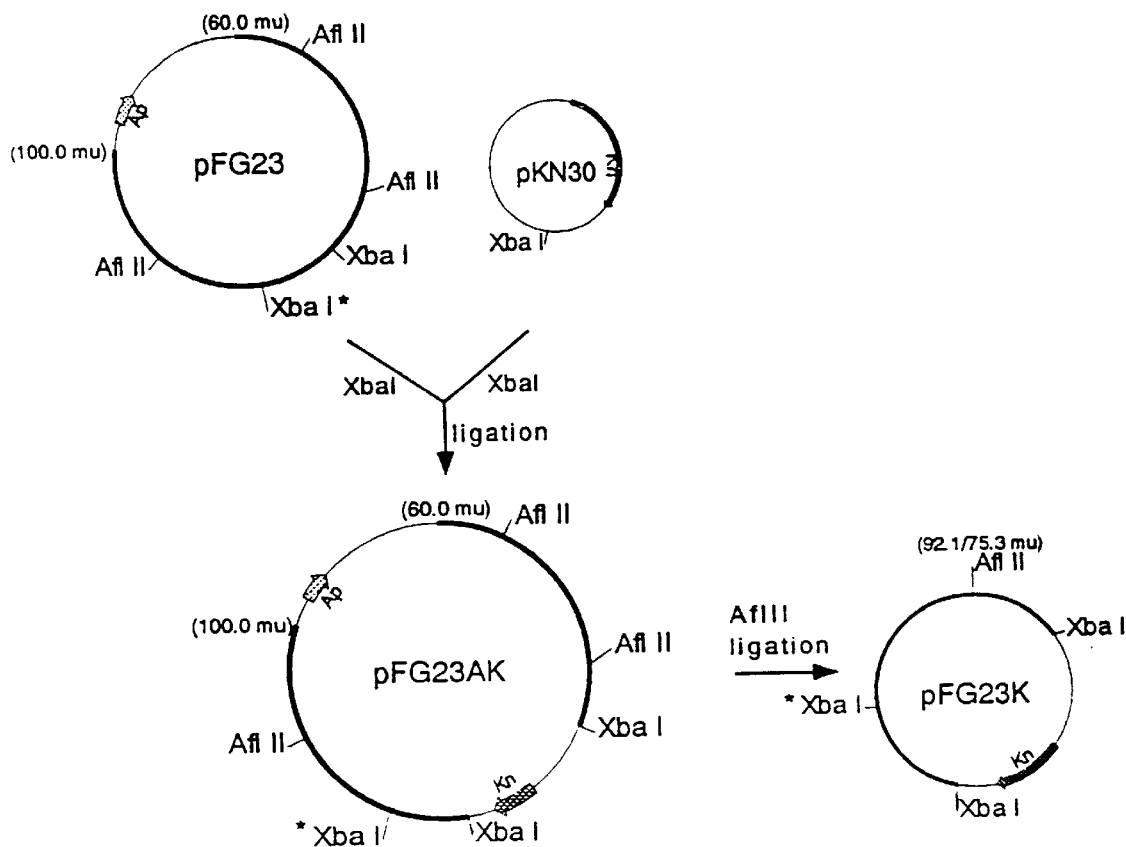
FIG. 2A is a diagrammatic representation of the structure and construction of vectors pFG23AK and pFG23K.
Figure 2B:
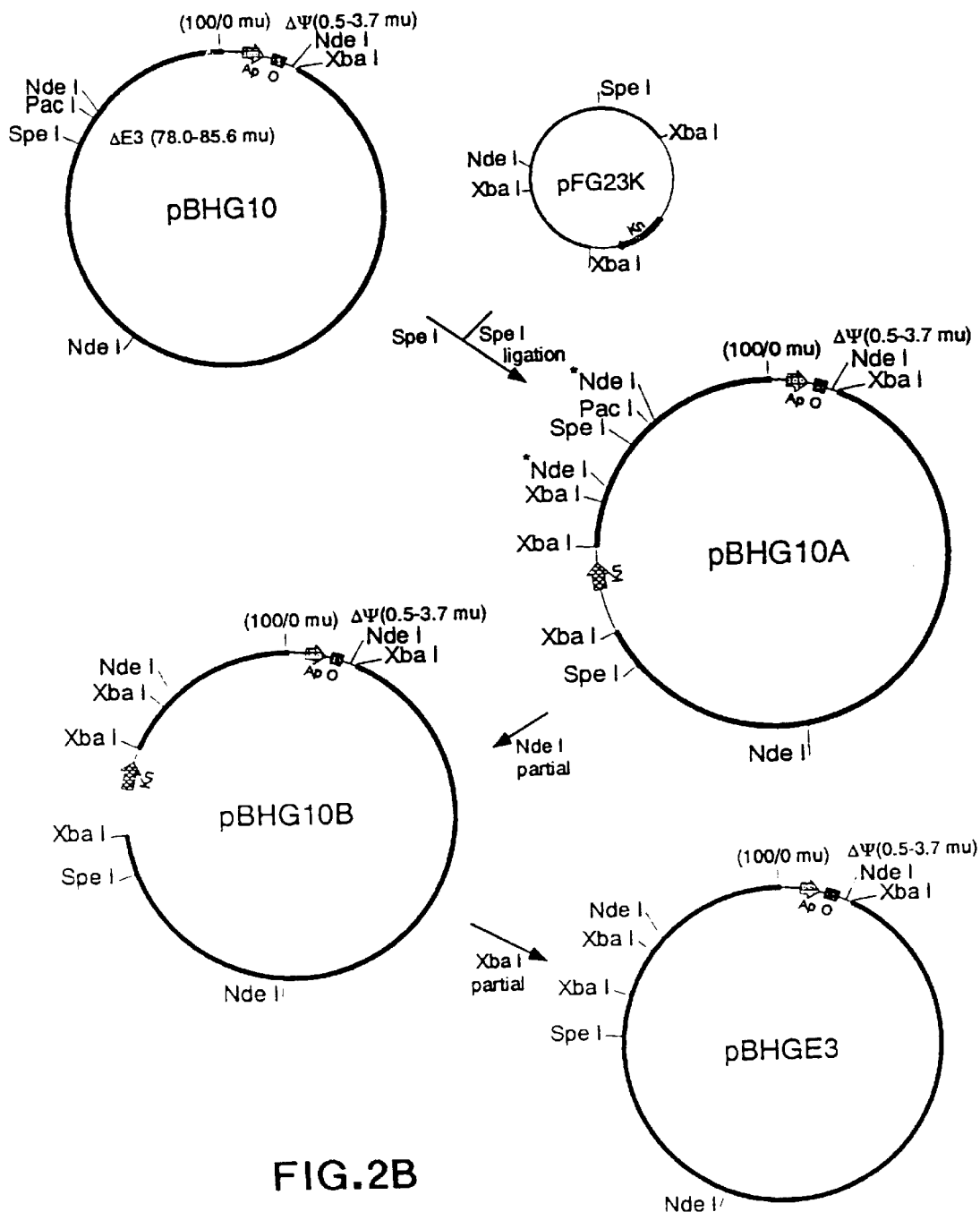
FIG. 2B is a diagrammatic representation of the structure and construction of vectors pBHG10A, pBHG10B and PBHGE3.

Additional Alterations to pBHG10: Insertion of Wild Type E3 Sequences and Substitution of the E3 Region with an Expanded Deletion Since for some applications it may be desirable to generate Ad vectors with intact wild type Ad5 E3 sequences, we reintroduced wild type E3 sequences into pBHG10 (FIG. 2). The first step involved construction of a plasmid carrying E3 sequences flanking a kanamycin resistance (Kn$^r$) gene to simplify insertion into pBHG10. The Ap$^r$ plasmid pFG23 (McKinnon, R. D., Bacchetti, S. & Graham, F. L. (1982) *Gene* 19: 33–42) was digested with XbaI, which cuts at position 28592 in Ad5 sequences (there is no cleavage at 30470 bp due to Dam methylation in the *E. coli* strain used) and ligated with XbaI-digested pKN30 (Lee, F. (1982) PH.D. Thesis, McMaster University, Hamilton, Ontario, Canada), generating pFG23AK (Ap$^r$ and Kn$^r$) (FIG. 2A). To remove extraneous Ad5 sequences and the Ap$^r$ gene, pFG23AK was digested with AflII and ligated, generating pFG23K.

The next step involved insertion of E3 sequences back into pBHG10 in the correct orientation (FIG. 2B). pBHG10 was digested with SpeI, which cuts only at 75.4 mu in Ad5 sequences, and ligated with pFG23K which had been linearized with SpeI, generating pBHG1OA which now contains the desired wild type E3 sequences in tandem with the previous E3 region containing the 2.69 kb deletion. To remove repeated sequences, pBHG1OA was partially digested with NdeI and religated, generating pBHG1OB. In the final step the Kn$^r$ segment was removed from pBHG1OB by partial XbaI digestion and religation, generating pBHGE3. Except for the presence of a wild type E3 region, pBHGE3 is identical to pBHG10, and is equally efficient for generation of Ad vectors with E1 substitution by cotransfection (unpublished).

Our analysis of the sequences in the E3 region of Ad5 led us to believe it might be possible to expand the 2.69 kb deletion present in pBHG10 to 3.13 kb. By utilizing the technique of polymerase chain reaction (PCR) and following a strategy very similar to that described above for the construction of pBHGE3 (FIG. 2), we created a 3.13 kb E3 deletion and introduced it into pBHG10. The resulting plasmid pBHG11 is identical to pBHG10 except for an expanded E3 deletion which removes sequences from 27865 to 30995 bp. Like pBHG10, pBHG11 contains a unique PacI restriction enzyme site in place of the deleted E3 sequences to permit insertion of foreign genes.

Example 3

Figure 3:
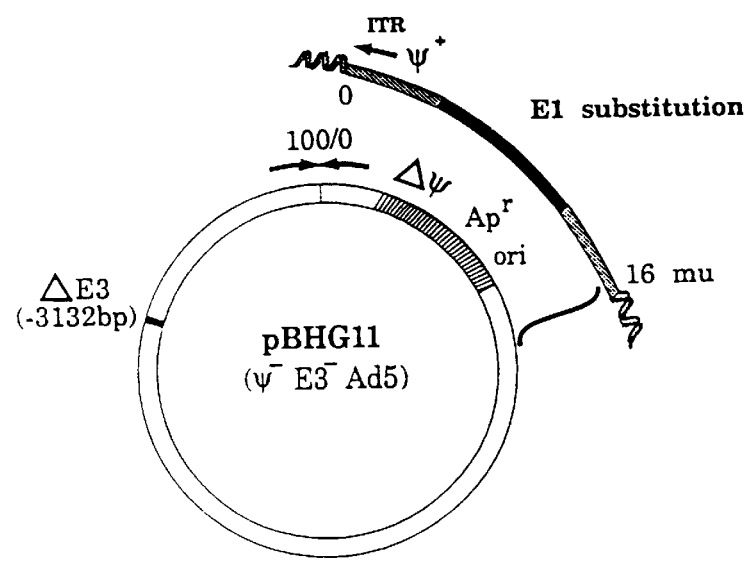
FIG. 3 is a diagrammatic representation of rescue using pBHG vectors.
Figure 3:
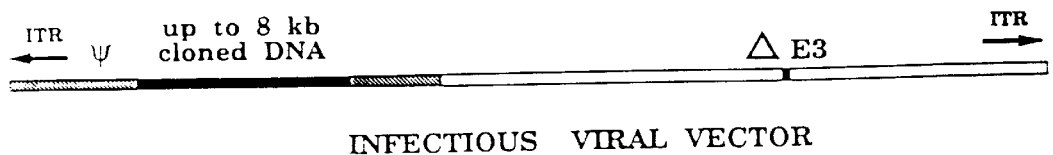

Construction of E1 Shuttle Plasmids for Use in Cotransfections with pBHG Vectors Plasmids pBHG10, pBHG11 and pBHGE3 were designed so that they would contain all the essential Ad5 sequences required to produce infectious virus upon transfection of 293 cells except for the packaging signal (194–358 bp) needed to encapsidate viral DNA into viral particles. To generate infectious viral vectors pBHG10, pBHG11, pBHGE3 or derivatives carrying an insert in E3 must be cotransfected into 293 cells with a second plasmid containing left end (E1) viral sequences including the packaging signal, as illustrated in FIG. 3. To maximize the capacity of the BHG vector system we required a plasmid with the largest possible E1 deletion for co-transfections with the BHG plasmids.

Figure 4:
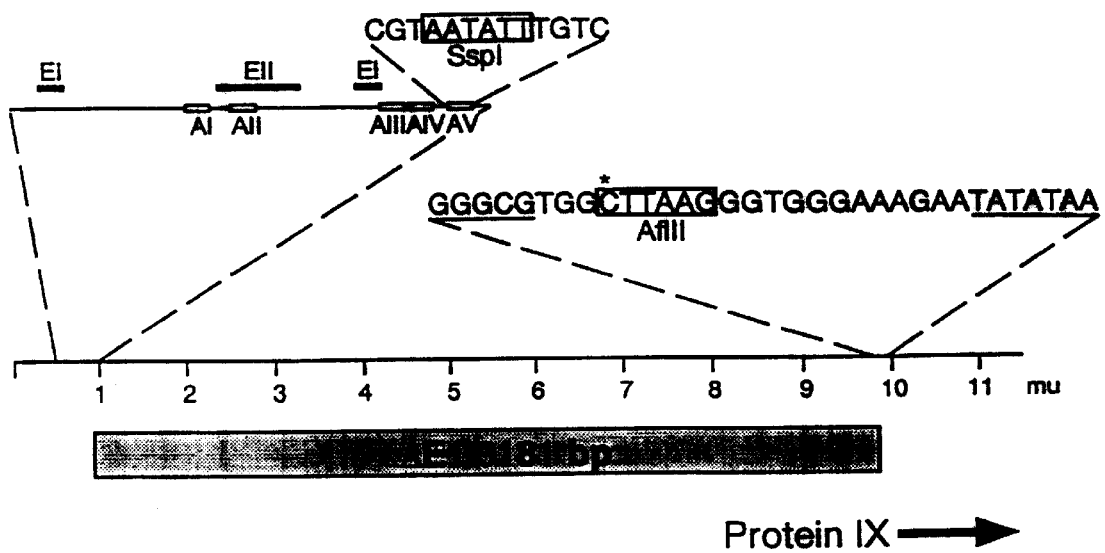
FIG. 4 is a diagrammatic representation of the structure and construction of a 3.2 kb E1 deletion, and two examples (pΔE1sp1A and pΔE1sp1B) of plasmids that contain said deletion.
Figure 4:
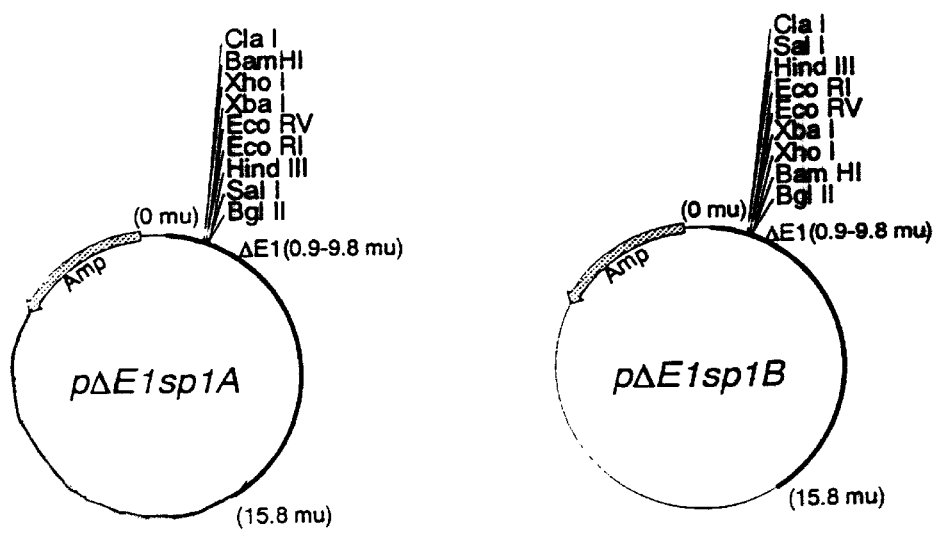

Our analysis of E1 sequences revealed that a deletion of approximately 3.2 kb could be created by removing the sequences between an Ssp I site at 339 bp and an Afl II site at 3533 bp (FIG. 4). This deletion does not interfere with the ITR (1–103 bp), the essential core packaging signal (194–358 bp) or coding sequences for protein IX but it does remove the sp1 binding site (3525–3530 bp) from the protein IX promoter. While this 3.2 kb E1 deletion does not interfere with the E1 enhancer region, it does remove the 3'-most, packaging element. The removal of this element has little or no effect on packaging.

Since the sp1 binding site is thought to be essential for protein IX expression, (Babiss, L. E. & Vales, L. D. (1991) *J. Virol.* 65: 598–605) it was reintroduced as a synthetic oligonucleotide which positioned the sp1 site 1 bp closer to the protein IX TATA box (FIG. 4).

Figure 5:
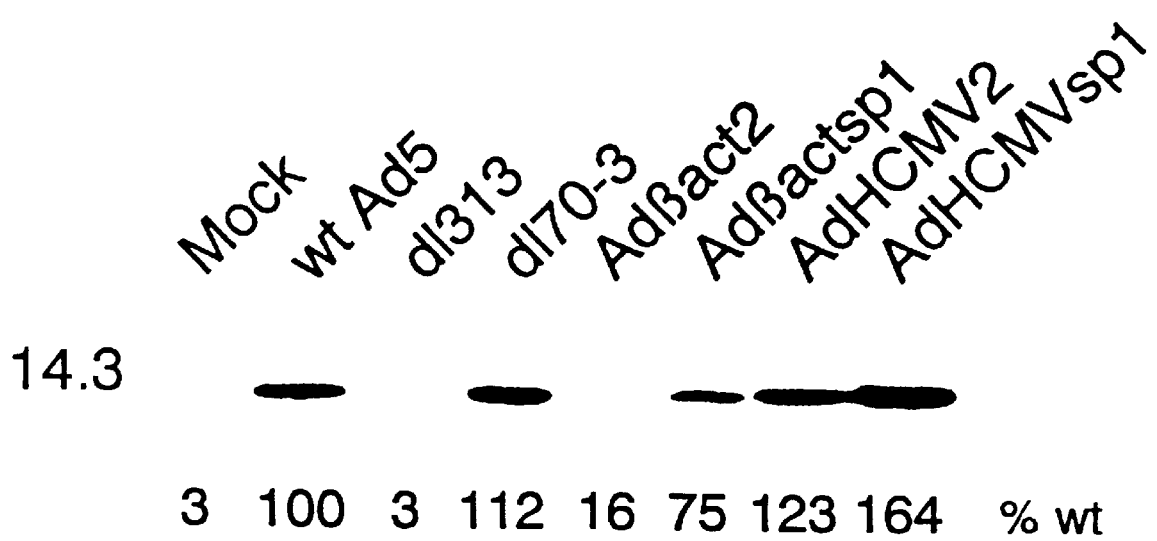
FIG. 5 illustrates the different levels of protein IX synthesized using plasmids having different E1 deletions with or without a reintroduced Ssp1 site.

To assess the effect of the 3.2 kb E1 deletion and the reintroduction of the sp1 binding site, we examined protein IX expression by immunoprecipitation. 293 cells were infected at 10 PFU/cell with viruses containing either no deletion in E1 (wild type Ad5), a 2.3 kb deletion extending into the protein IX gene (dl313), the 3.2 kb deletion described above (dl70-3), the 3.2 kb deletion containing the HCMV (AdHCMV2) or β-Actin (AdβAct2) promoters in the E1 antiparallel orientation or the 3.2 kb deletion containing the HCMV (AdHCMVsp1) or β-Actin (AdβActsp1) promoters with the reintroduced sp1 binding site. After labelling with [$^{35}$S]-methionine cell extracts were harvested, samples were immunoprecipitated with anti Ad2 protein IX antibodies and run on a 12% SDS PAGE gel. The results (FIG. 5) indicate that variable levels of protein IX were expressed depending on the sequences upstream from the protein IX gene but with the sp1 site present there was at most a 25% reduction compared to wild type Ad5.

Figure 6:
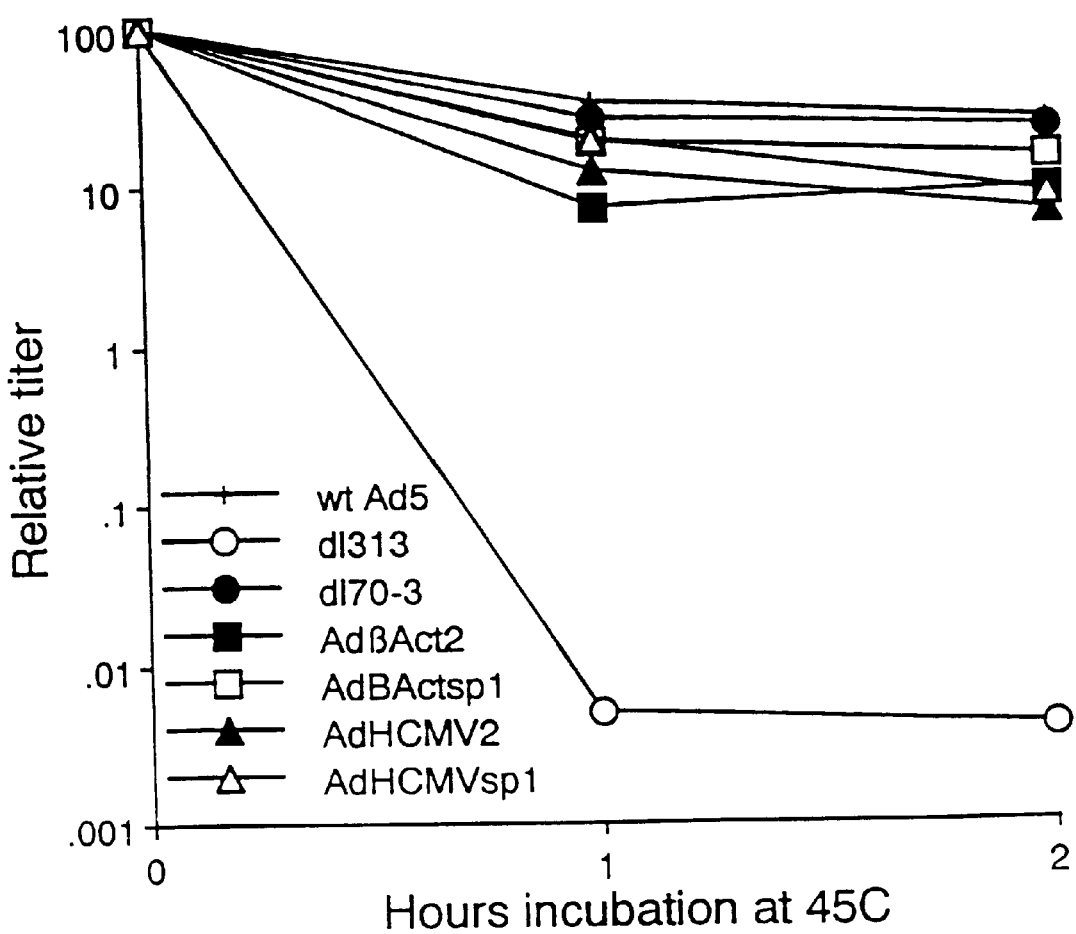
FIG. 6 illustrates heat stability of viruses with the 3.2 kb E1 deletion with or without a reintroduced Ssp1 site.

Because protein IX is known to affect the heat stability of virus particles we examined the heat stability of wild type Ad5 compared to dl313, dl70-3, AdHCMV2, AdβAct2, AdHCMVsp1 and AdβActsp1. Stocks of these viruses were titered prior to and after incubation at 45° C. for 1 and 2 hours. Of the six viral mutants tested only dl313 differed significantly in heat lability from wild type (FIG. 6). Even AdβAct2, which produces only 16% of wild type levels of protein IX (FIG. 5) was as resistant to heat inactivation as was wild type virus. This indicates that Protein IX is likely made in excess during viral infection. We have also found that viruses containing the 3.2 kb E1 deletion replicate in 293 cells to the same final titers as wild type Ad5 (data not shown).

With the verification that the growth characteristics and stability of viruses with the 3.2 kb E1 deletion were not affected it was decided to incorporate this deletion into plasmids pΔElsp1A and pΔElsp1B for use in cotransfections with the BHG plasmids (FIG. 4). These plasmids contain various restriction sites to facilitate the insertion of foreign genes.

The invention also includes a vector that includes a fragment or fragments of plasmid pBR322 which includes both an ampicillin resistance and the pBR322 origin of replication (which enables said vector to be replicated in cells wherein pBR322 is capable of being replicated), and an insert between early region 4 (E4) and the right inverted terminal repeat, and a deletion of E1 sequences from position 188 to or near the AflIII sequence at position 3533, and cloning sites for the insertion of a foreign nucleic acid.

Testing the Efficiency and Capacity of the pBHG Vectors

To assess the ability of the BHG plasmids to generate infectious viral vectors, cotransfections with various left end plasmids were performed and it was found that the efficiency of rescue was comparable to that obtained with pJM17 (data not shown).

Figure 7:
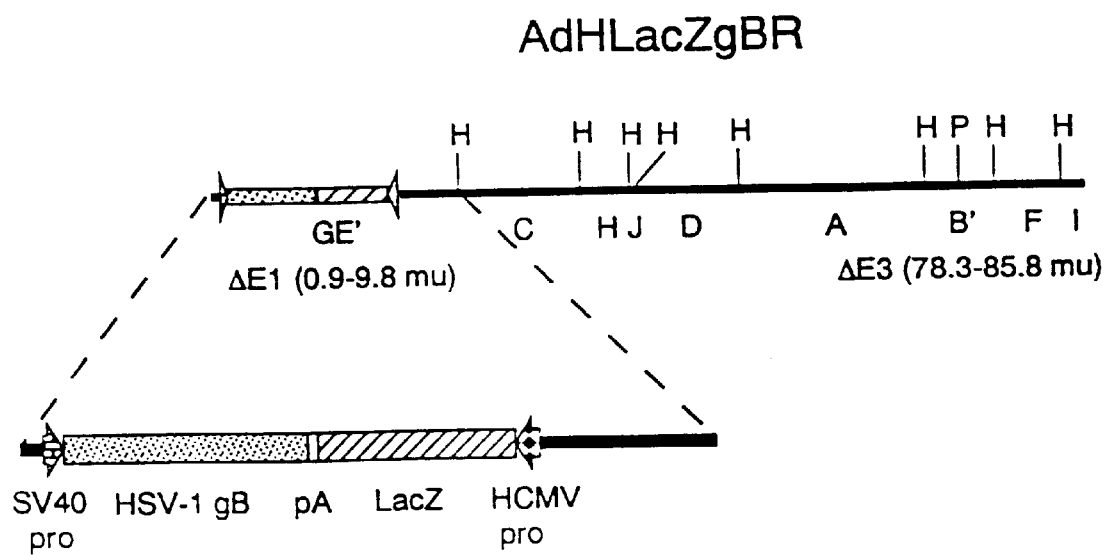
FIG. 7 illustrates the construction and rescue of a 7.8 kb insert using pBGH10.

The use of pBHGE3, pBHG10 or pBHG11 combined with the 3.2 kb deletion in E1 should permit rescue of inserts of approximately 5.2, 7.9 and 8.3 kb respectively into viral vectors. In order to test the capacity of the BHG system we constructed an insert of 7.8 kb consisting of the lacZ gene driven by the human cytomegalovirus immediate early promoter and the herpes simplex virus type 1 (HSV-1) gB gene driven by the SV40 promoter in the 3.2 kb E1 deletion (FIG. 7). Following cotransfection of 20–60 mm dishes of 293 cells, 10 with 5 μg each of pBHG10 and pHlacZgBR and the other half with 10 μg of each, one plaque was obtained. This was isolated, expanded, analyzed by restriction digest with HindIII and found to have the expected restriction pattern. The isolate designated AdHlacZgBR was found to express both lacZ and HSV-1 gB at levels comparable to that obtained with vectors containing single inserts of these genes (data not shown).

Example 4

Additional Shuttle Plasmids

A shuttle vector, pABS.4, was used in the construction of a double recombinant containing lacZ in the E3 deletion and firefly luciferase in the E1 deletion. The construction of this vector further illustrates the use of the shuttle vectors as well as double recombinants.

Figure 8A:
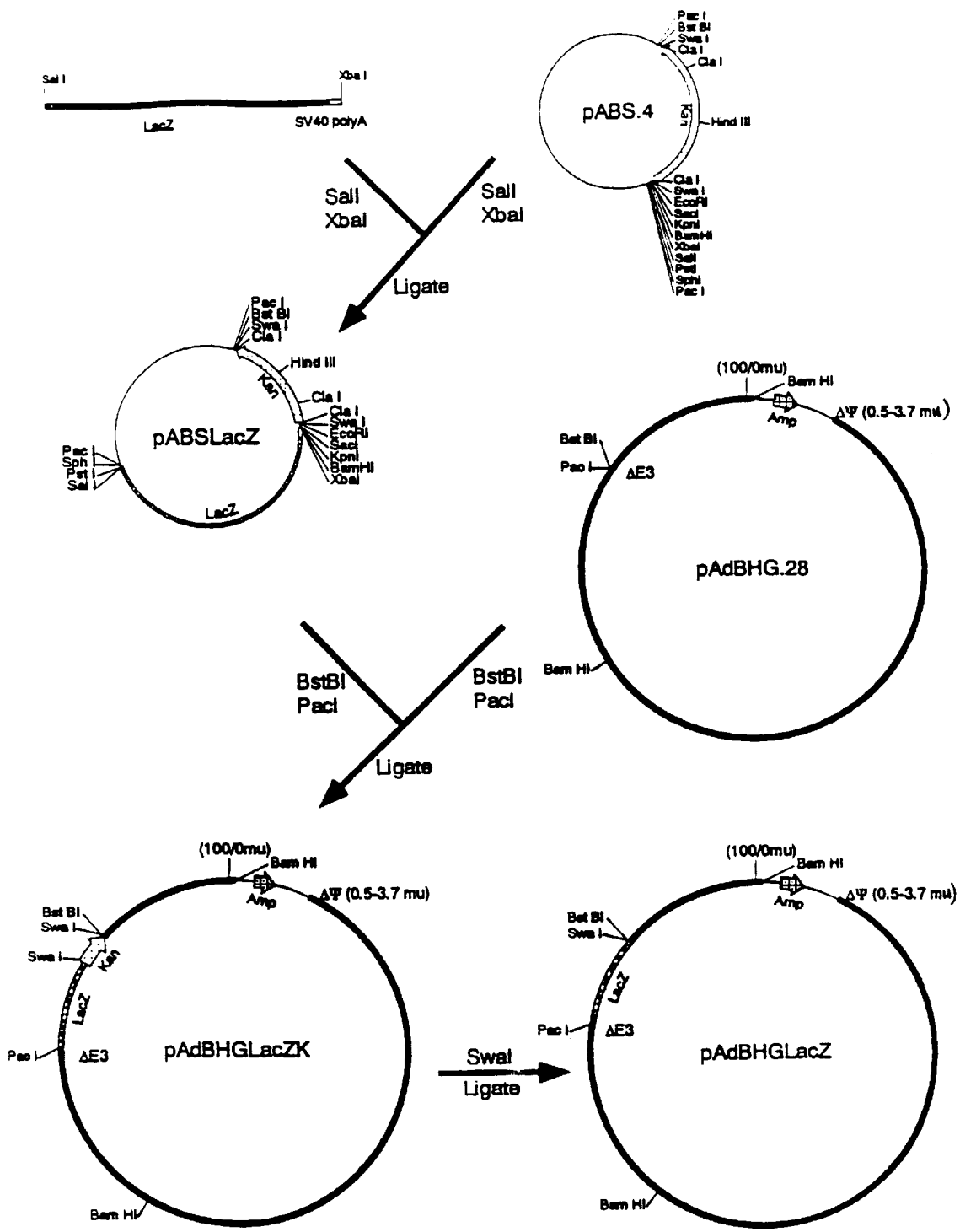
FIG. 8A is a diagrammatic representation of the structure and construction of vectors pABSLacZ, pADBHGLacZK, and pAdBHGLacZ.
Figure 8B:
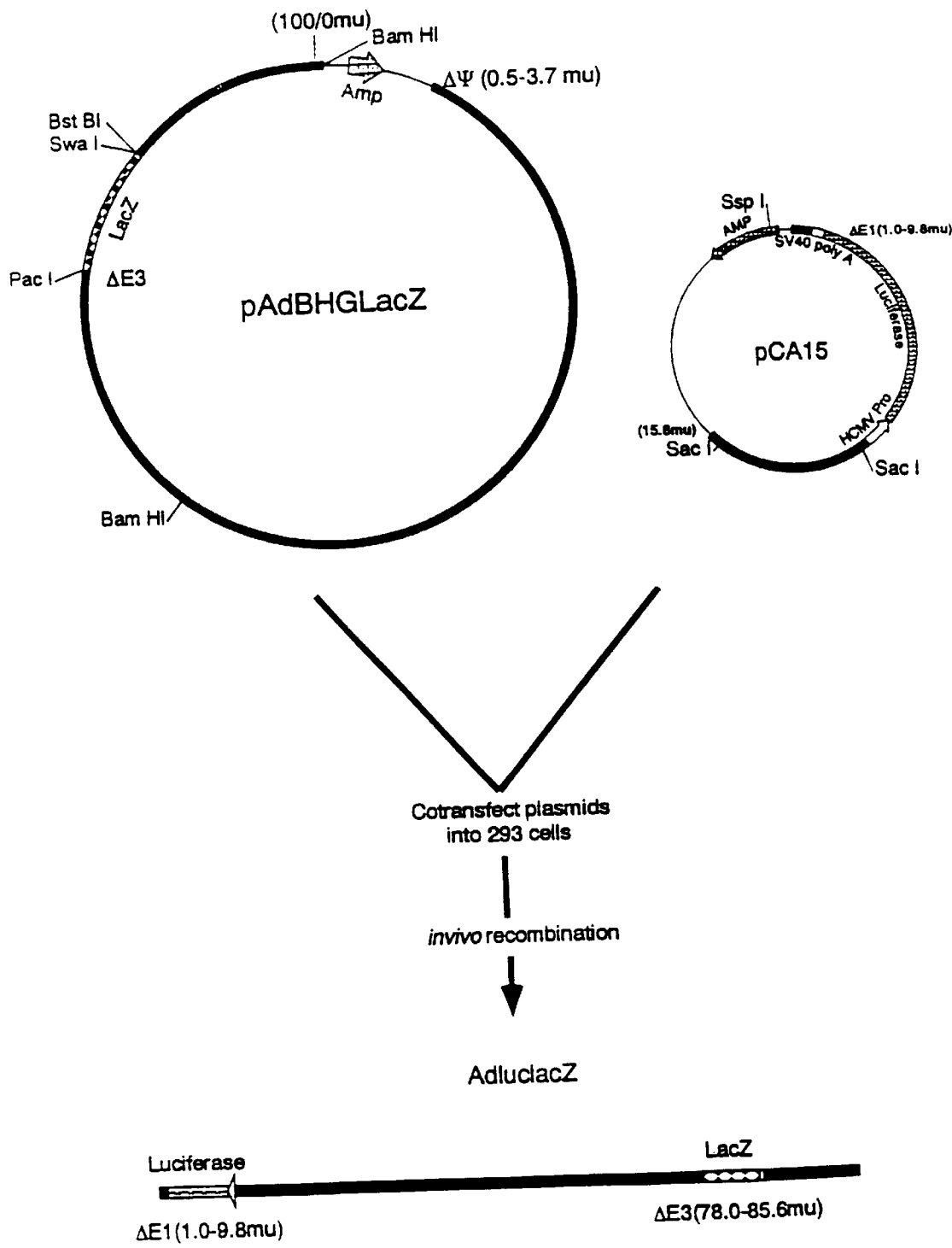
FIG. 8B is a diagrammatic representation of the structure and construction of nucleic acid encoding AdluclacZ.

The strategy for the construction of this vector is presented in FIG. 8. First the lacZ gene with the SV40 poly A signal was inserted between the SalI and XbaI sites in the cloning region of pABS.4, generating pABSLacZ. FIG. 8A. In the next step pABSLacZ was digested with PacI and BstBI generating a fragment containing the LacZ gene and the Kanamycin resistance gene (Kan$^r$). This fragment was then inserted between the PacI and BstBI sites of pAdBHG.28, in the E3 parallel orientation, generating pAdBHGLacZK. Because double antibiotic selection was used, screening for the desired plasmid containing the lacZ insert was trivial. Finally pAdBHGLacZK was digested in SwaI to remove the Kan$^1$ gene generating pAdBHGLacZ. pAdBHGLacZ are grown and used in cotransfection with pCA15, a plasmid containing Ad5 left end sequences with firefly luciferase under the control of the human cytomegalovirus immediate early gene (HCMV) promoter in place of most of E1. FIG. 8B. pAdBHGLacZ can be used in cotransfections with virtually any E1 derived construct to make vectors with a variety of combinations of lacZ in E3 and foreign gene inserts or mutations in E1.

Figure 9:
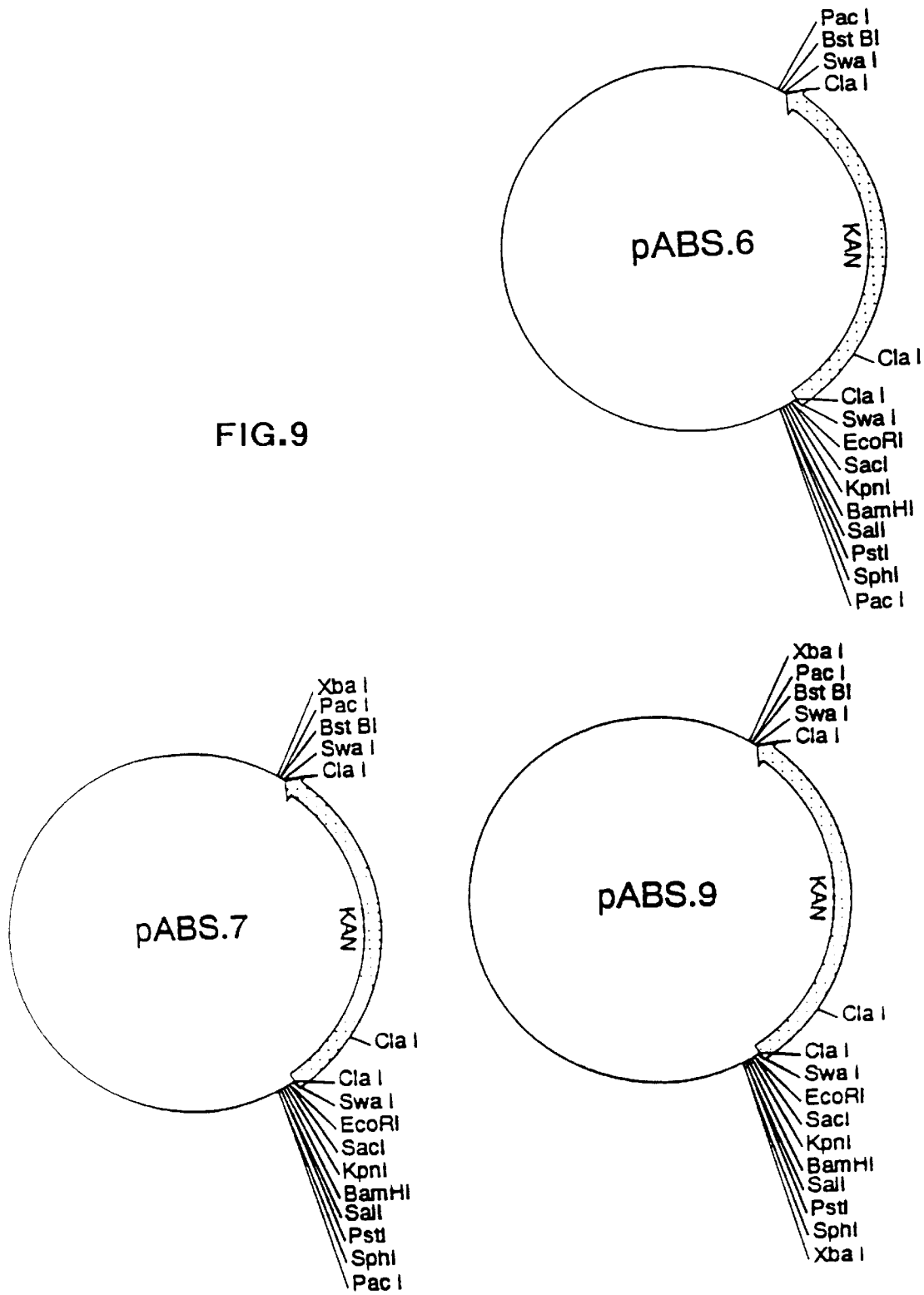
FIG. 9 is a diagrammatic representation of the plasmids pABS.6, pABS.7, and pABS.9.
Figure 10:
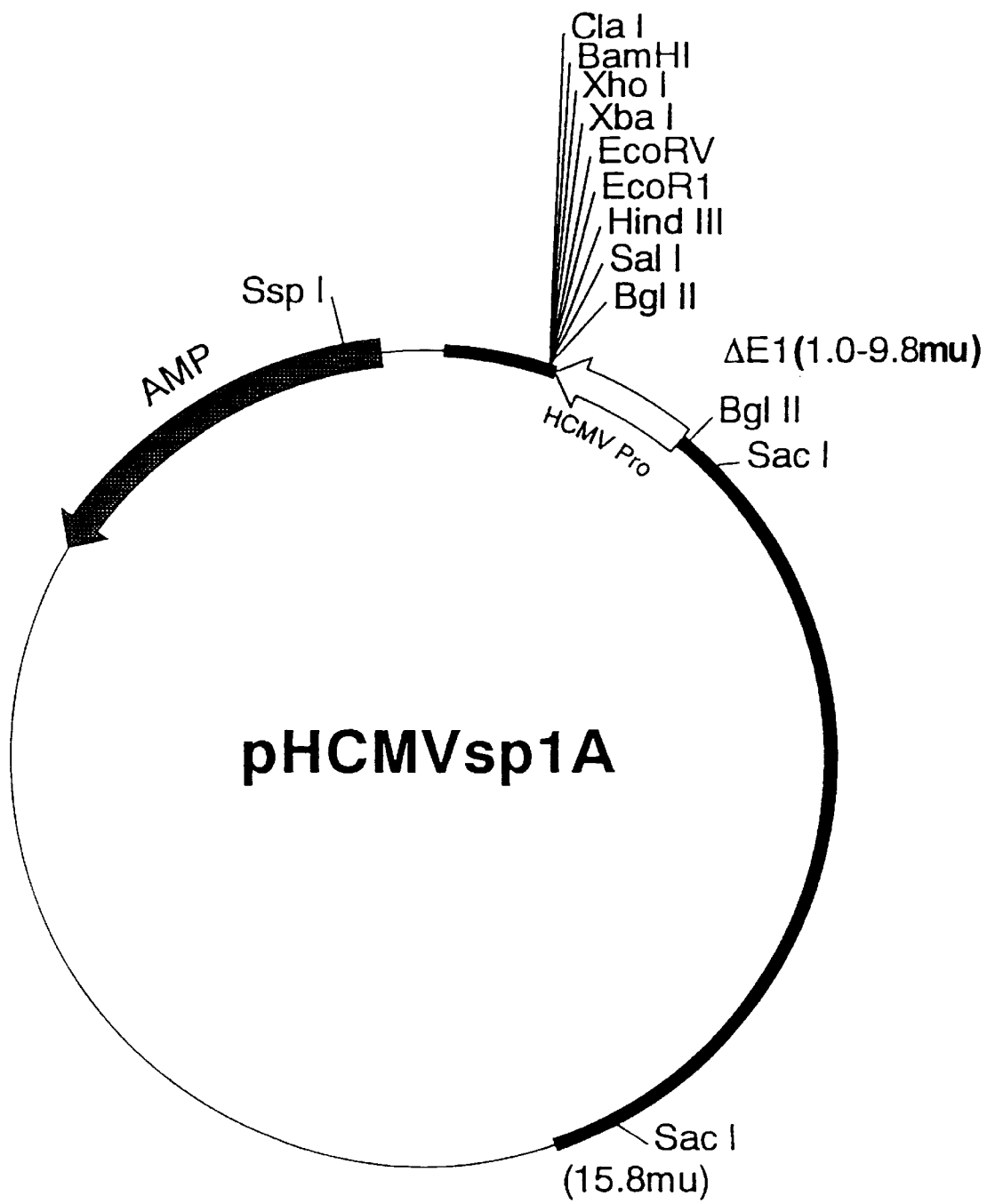
FIG. 10 is a diagrammatic representation of the shuttle plasmid pHCMVsp1A generated by insertion of the human cytomegalovirus immediate early gene promoter ("HCMV Pro") into the Bgl II site of pΔE1sp1A.
Figure 11:
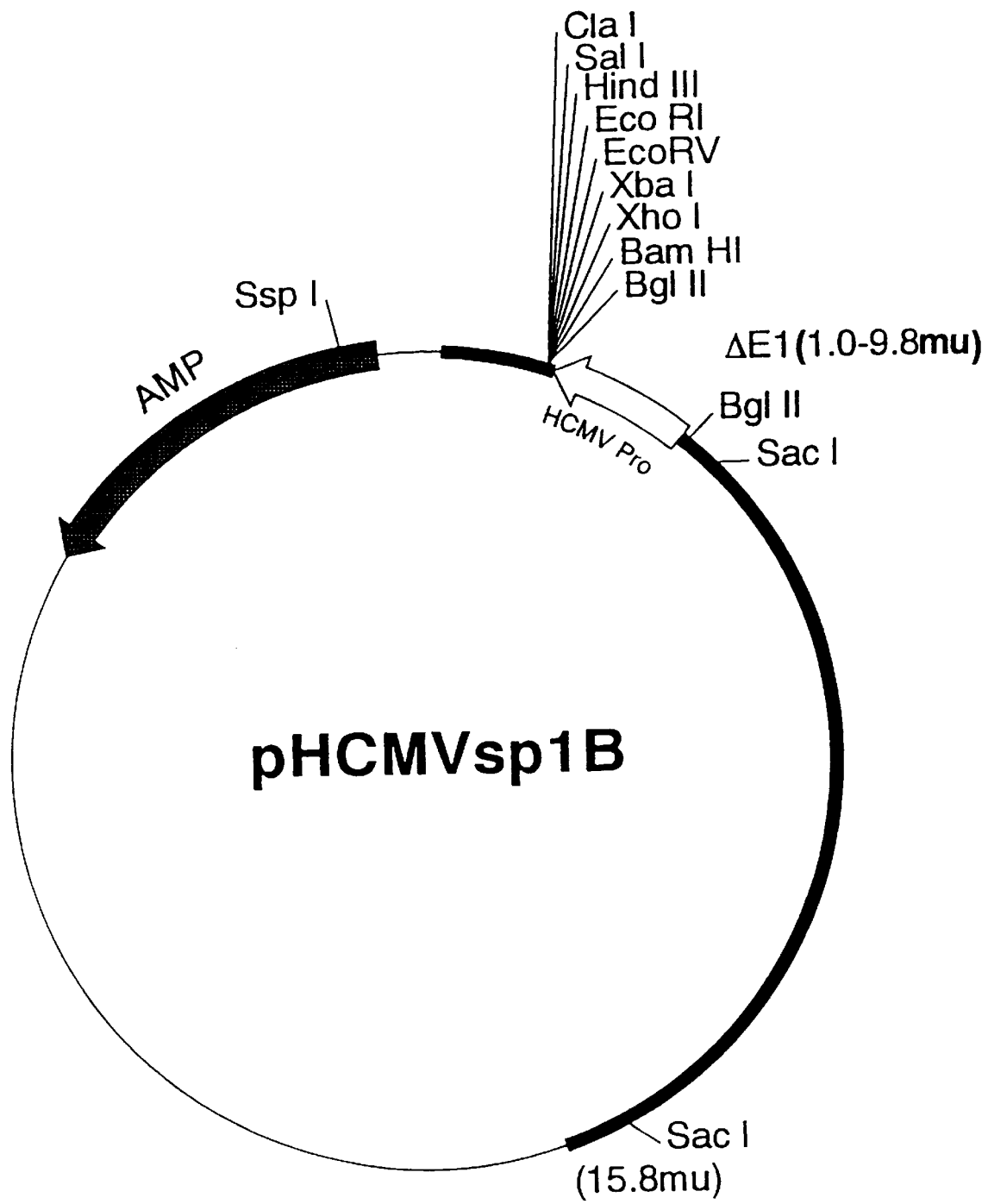
FIG. 11 is a diagrammatic representation of the shuttle plasmid pHCMVsp1B generated by insertion of the HCMV Pro DNA into the Bgl II site of pΔE1sp1B.
Figure 12:
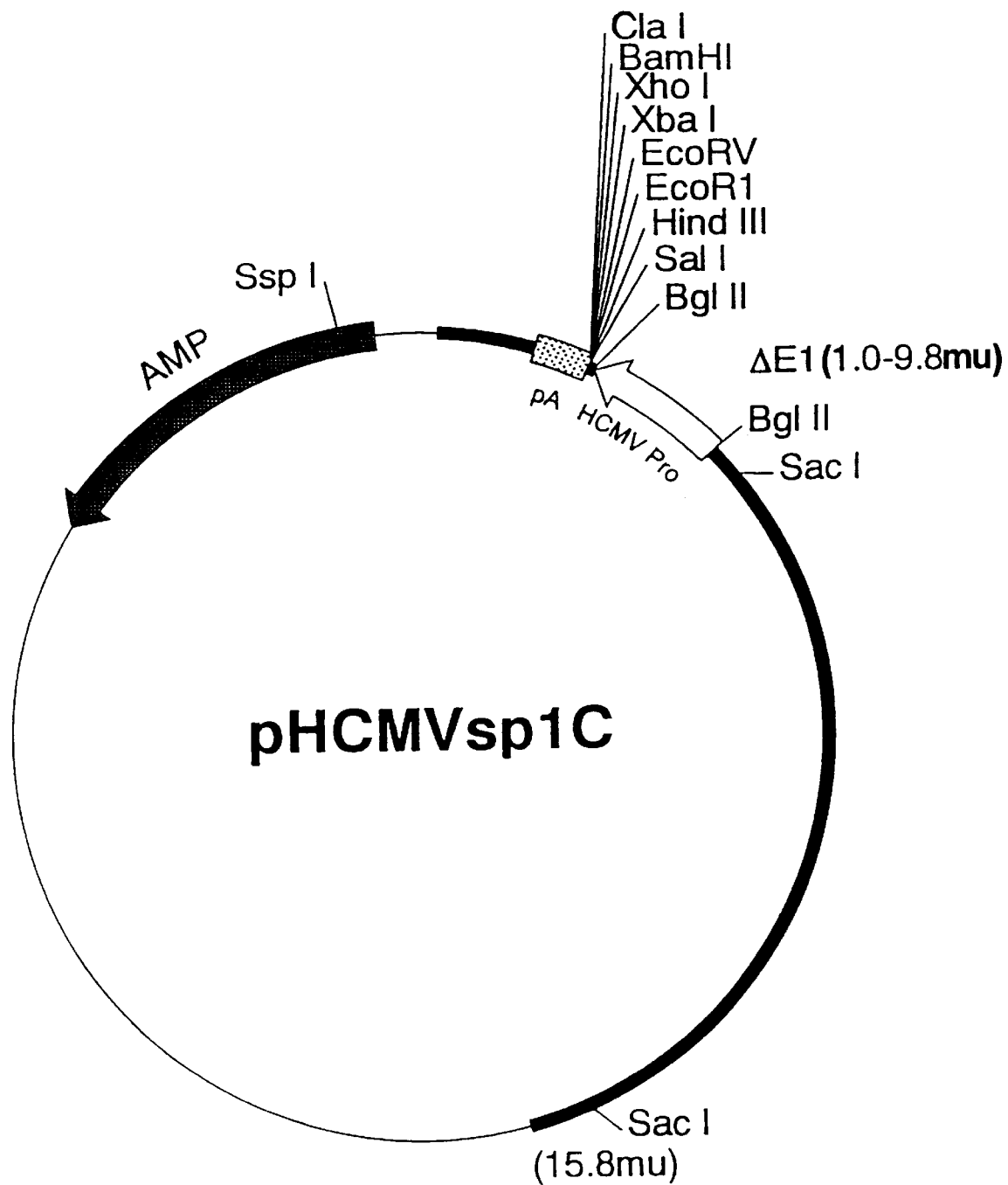
FIG. 12 is a diagrammatic representation of the shuttle plasmid pHCMVsp1C generated by the insertion of DNA encoding the SV40 polyadenylation signal (SV40pA) into the Cla I site of pHCMVsp1A.
Figure 13:
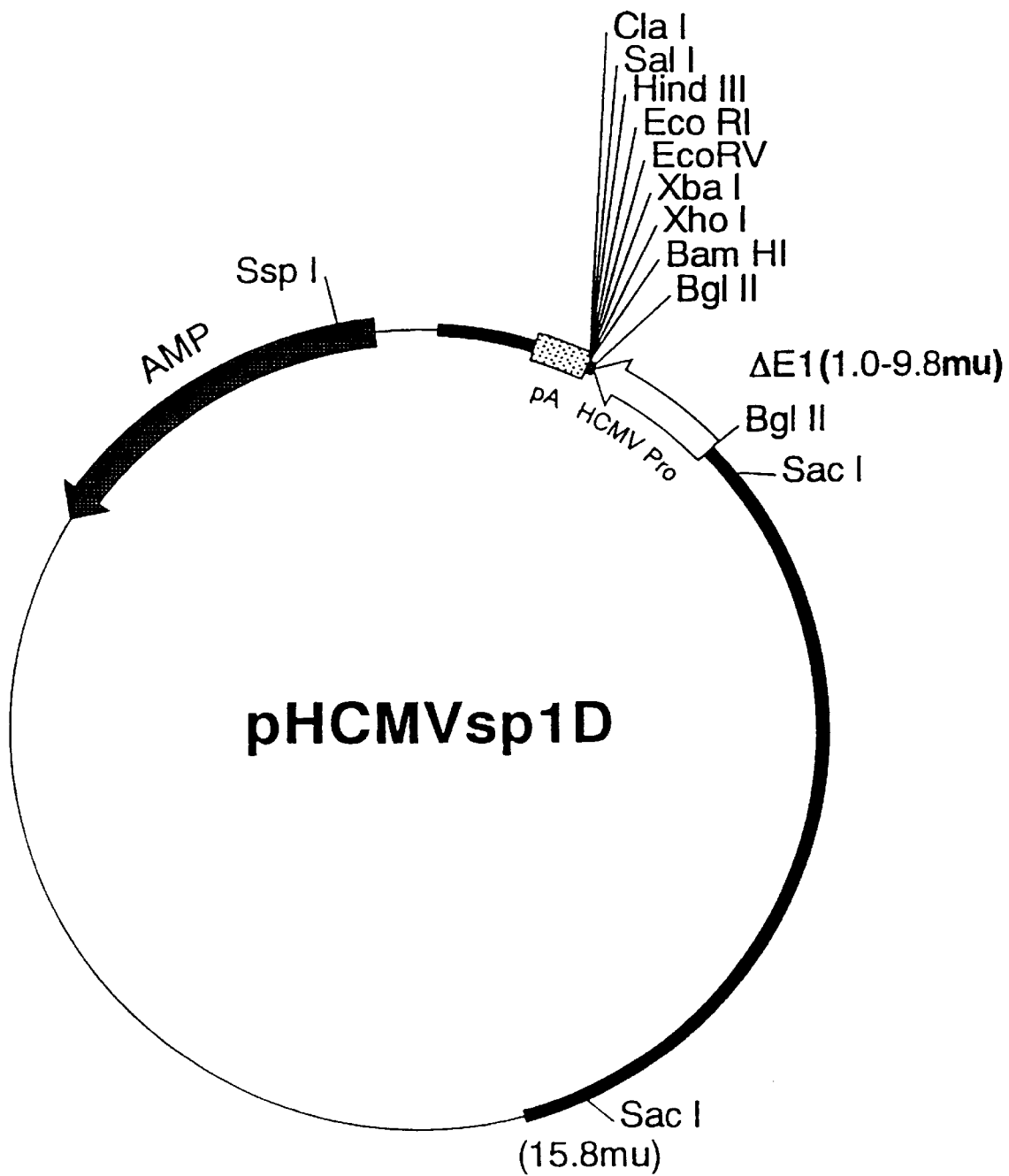
FIG. 13 is a diagrammatic representation of the shuttle plasmid pHCMVsp1D generated by the insertion of DNA encoding the SV40 polyadenylation signal into the Cla I site of pHCMVsp1B.

We developed shuttle vectors pABS.6 pABS.7 and pABS.9 to simplify the introduction of inserts into the E3 deletion in the pAdBHG plasmids. FIG. 9. They are used to facilitate transfer of foreign genes into the pAdBHG series of plasmids as follows: gene sequences are inserted into either pABS.7 or pABS.9 using cloning sites SphI, PstI, SalI, BamHI, KpnI, SacI, or EcoRI. The shuttle plasmid is then cut with one or two combinations of XbaI, PacI or BstBI and the Kan containing fragment is inserted into the Amp$^r$ pAdBHG plasmid making use of Amp+Kan double resistance to select for bacterial transformants carrying the desired plasmid. Subsequently the Kan$^r$ gene is removed by digestion with ClaI or SwaI and ligation. Finally the plasmid is "rescued" into infectious Ad viral vectors by cotransfection of 293 cells with an appropriate plasmid containing E1 sequences.

A number of shuttle plasmids have been constructed that can be used for cotransfections with vectors of the pGBH series. These are listed in Table I; see also FIGS. 10–13. An E1 shuttle plasmid having a packaging signal inserted between early region 4 (E4) and the right inverted terminal repeat (ITR) is specifically part of the subject matter of the invention.

TABLE 1

Additional E1 Shuttle Plasmids for Cotransfection with pBHG Vectors

| plasmid | regulatory sequences | net deletion | cloning sites |
| --- | --- | --- | --- |
| pXCJL1 | — | 2.88 kg | X-B-Xh-S-C |
| pXCJL2 | — | 2.88 kb | C-S-Xh-B-X |
| PAE1sp1A | — | 3.19 kg | C-B-Xh-X-EV-E-H-S-Bg |
| pAE1sp1B | — | 3.19 kg | C-S-H-E-EV-X-Xh-B-Bg |
| pHCMVsp1A | HCMV (L) | 2.81 kb | C-B-Xh-X-EV-E-H-S |
| pHCMVsp1B | HCMV (L) | 2.81 kb | C-S-H-E-EV-X-Xh-B |
| pHCMVsp1C | HCMV(L)/SV40pA | 2.66 kb | C-B-Xh-X-EV-E-H-S |
| pHCMVsp1D | HCMV(L)/SV40pA | 2.66 kb | C-S-H-E-EV-X-Xh-B |
| pCA3 | HCMV(L)/SV40pA | 2.66 kb | B-Xh-X-EV-E-H-S |
| pCA4 | HCMV(L)/SV40pA | 2.66 kb | S-H-E-EV-X-Xh-B |
| pCA13 | HCMV(R)/SV40pA | 2.66 kb | S-H-E-EV-X-Xh-B |
| pCA14 | HCMV(R)/SV40pA | 2.66 kb | B-Xh-X-EV-E-H-S |
| pBActsp1A | βActin(L) | 1.74 kb | C-B-X-EV-E-H-S |
| pBActsp1B | βActin(L) | 1.74 kb | C-S-H-E-EV-X-B |
| pCA1 | βActin(L)/SV40pA | 1.58 kb | S-H-E-EV-X-B |
| pCA2 | βActin(L)/SV40pA | 1.58 kb | B-X-EV-E-H-S |
| pMLPsp1A | MLP(R) | 2.23 kb | B-X-EV-E-H-S-Bg |

X: XbaI, B: BamHI, Xh: XhOI,S: SalI, C; ClaI, EV: EcoRV, E: EcoRI, H: HindIII, Bg: BglII

We claim:

1. A kit for making an adenovirus vector comprising nucleic acid sequences of a first plasmid and a second plasmid, said kit comprising a first and a second plasmid:
   (a) wherein said first plasmid comprises:
      (i) a modified adenovirus genome, wherein said genome comprises a modification within early region 1 (E1) that comprises a deletion of a packaging signal of the early region 1 which renders said first plasmid incapable of forming viable viral particles in host cells, by eliminating susceptibility of adenoviral sequences encoded by said first plasmid to being encapsidated into a viral particle, but does not affect the ability of the adenovirus genome to replicate, and
      (ii) at least one nucleic acid sequence for (A) encoding antibiotic resistance and (B) replication of said first plasmid in host cells; and
   (b) wherein said second plasmid is an E1 shuttle plasmid, which comprises at least one nucleic acid sequence comprising adenovirus genome E1 region sufficient to rescue said first plasmid via recombination of said first plasmid and said second plasmid to produce said adenovirus vector.

2. The kit according to claim 1, wherein the adenovirus genome within said first plasmid is that of adenovirus 5 (Ad5).

3. The kit according to claim 1, wherein said modification in E1 in said first plasmid is a deletion that comprises the E1A region.

4. The kit according to claim 1, wherein the deleted E1 region in said first plasmid spans nucleotides 188 to 1339.

5. The kit according to claim 1, wherein said second plasmid comprises a deletion in the E1 region starting from a position rightward of an adenoviral packaging signal and extending to a position leftward of adenoviral coding sequences for pIX.

6. The kit according to claim 1, wherein an Sp1 site at position 3525 that was deleted from said second plasmid is reintroduced by inserting a synthetic oligonucleotide that includes an Sp1 site in said second plasmid.

7. The kit according to claim 1, wherein the E1 deletion in said second plasmid is complemented by viral E1 sequences expressed by 293 cells when said vector is packaged in 293 said cells.

8. The kit according to claim 1, further comprising a deletion within early region 3 (E3) in said first plasmid, wherein said E3 deletion does not inhibit the expression of sequences necessary for viral replication, packaging, viability, or infectivity and wherein said deleted E3 sequences are optionally replaced by foreign DNA.

9. The kit according to claim 1, wherein said first plasmid further includes restriction enzyme cleavage sites for the insertion of a nucleic acid sequence.

10. The kit according to claim 1 wherein said second plasmid comprises the approximately 340 left end base pairs of the adenovirus type 5 genome, said second plasmid further comprising the left end inverted terminal repeat sequences of said genome and the packaging signal sequences thereof, said second plasmid also comprising a gene sequence of up to about 8 kilobases foreign to said adenovirus vector and to said viral genome, and wherein additional nucleotide sequences sufficient for recombination between said first plasmid and said second plasmid are present on the right side of said foreign sequence.

11. The kit according to claim 1 wherein said first plasmid includes at least one nucleic acid sequence of plasmid pBR322 of section 1(a)(ii) which encodes an ampicillin resistance gene, and also a pBR322 origin of replication which enables said first plasmid to be replicated in cells wherein pBR322 is replicated.

12. The kit according to claim 1 comprising a first plasmid encoding an adenoviral genome having, in addition to a deletion of a packaging signal, a deletion of the E3 region or an insertion of foreign DNA in the E3 region, or a substitution of E3 sequences by foreign DNA, and a second plasmid comprising a left end inverted terminal repeat sequence, a packaging signal, and either a complete E1 region or a deletion of E1 sequences, or a substitution of E1 sequences with foreign DNA such that recombination between said first and said second plasmids results in an adenoviral vector having a deletion selected from the group consisting of the E1 region only, the E3 region only, and a combined deletion of the E1 and E3 regions, said vector being susceptible to being packaged in 293 cells into a viral particle that is capable of infecting host cells and of expressing said foreign DNA.

13. The kit according to claim 1 wherein said first plasmid comprises at least one nucleic acid sequence of plasmid pBR322 which encodes an ampicillin resistance and also a pBR322 origin of replication, wherein said plasmid is further modified to contain an insert between early region 4 (E4) and the right inverted terminal repeat, which plasmid further has a deletion of the packaging signal and all or part of the E1 sequences starting from position 188 and extending to a position leftward of the coding sequence for pIX, wherein said plasmid contains cloning sites for the insertion of a foreign nucleic acid.

14. The kit according to claim 1 wherein said E1 shuttle plasmid comprising said sequence derived from the adenovirus genome E1 region comprises a packaging signal, and wherein said sequence from the adenovirus genome E1 region recombines with the first plasmid according to claim 1 upon cotransfection into a host cell of said E1 shuttle plasmid and said first plasmid.

15. The kit according to claim 1 wherein the sequence of the second plasmid comprises a foreign nucleic acid sequence within the sequence derived from the adenovirus genome E1 region.

16. The kit according to claim 1 wherein said sequence of the first plasmid comprises foreign nucleic acid sequences within the E3 region of the modified adenovirus genome.

17. The kit according to claim 1 wherein said first plasmid comprises nucleic acid sequences derived from an E3 shuttle plasmid selected from the group consisting of pABS.4, pABS.6, pABS.7, and pABS.9.

18. The kit according to claim 8, wherein the E3 deletion in said first plasmid comprises positions 27865–30995 of the Ad5 genome.

19. The kit according to claim 14 wherein said E1 shuttle plasmid is selected from the group consisting of pΔE1sp1A and pΔE1sp1B.

20. The kit according to claim 14 wherein said E1 shuttle plasmid is selected from the group consisting of pHCMVsp1A, pHCMVsp1B, pHCMVsp1C, and pHCMVsp1D.

21. The kit according to claim 14 wherein said E1 shuttle plasmid is selected from the group consisting of pxCJL1, pXCJL2, pCA1, pCA2, pCA3, pCA4, pCA13, and pCA14.

22. The kit according to claim 14 wherein said E1 shuttle plasmid further comprises a foreign nucleic acid sequence within the sequence derived from the adenovirus genome E1 region.

23. A method for introducing and expressing a foreign nucleic acid sequence in a host cell, comprising:

(a) introducing into a mammalian host cell a first plasmid comprising a modified adenovirus genome having a modification within early region 1 (E1) sufficient to render said first plasmid unable to form viable viral particles in mammalian host cells, said modification eliminating susceptibility of said first plasmid to being encapsidated into a viral particle, said first plasmid further comprising at least one nucleic acid sequence for (A) encoding antibiotic resistance and (B) for replication of said modified adenovirus genome in bacterial host cells, and (b) introducing into said host cell recited in (a), an E1 shuttle plasmid that contains a sequence comprising adenovirus genome E1 region, comprising a packaging signal, and a nucleic acid sequence comprising a coding sequence having an open reading frame inserted into the E1 region and comprising sequences that regulate the expression of said open reading frame;

(c) isolating virus particles wherein said first plasmid has recombined with said shuttle plasmid to yield a recombinant modified viral genome containing elements of said first plasmid plus the packaging signal and the inserted nucleic acid sequence of the E1 shuttle plasmid;

(d) introducing said recombinant modified viral genome into a host cell; and (e) expressing the coding sequences contained in said modified recombinant viral genome.

24. The kit according to claim 16 wherein said sequence of the first plasmid comprises sequences that regulate the expression of said foreign nucleic acid sequence.

25. The kit according to claim 14 wherein said E1 shuttle plasmid comprises sequences that regulate the expression of said foreign nucleic acid sequence.

26. A plasmid that comprises a modified Ad5 genome, selected from the group consisting of: pBHGE3, pBHG9, pBHG10, pBHG10B and pBHG11.

27. A method for making an infectious adenoviral vector by recombining two plasmids, neither of which separately comprises sufficient sequences to produce an infectious adenoviral vector which comprises: infecting a cell with: (a) a first plasmid comprising adenoviral sequences in which adenoviral packaging sequences have been deleted, such that said first plasmid encodes a viral genome which cannot be packaged; and (b) a second plasmid comprising sufficient adenoviral sequences, upon recombination with sequences in said first plasmid, to reconstitute said deleted adenoviral packaging sequences in said first plasmid to produce an infectious adenoviral vector.

* * * * *

SEQUENCE LISTING

<160> NUMBER OF SEQ ID NOS: 2

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Sequence
      junctions of E1 deleted adenovirus

<400> SEQUENCE: 1
cgtaatattt gtc                                                      13

```
<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Sequence
      junctions of E1 deleted adenovirus

<400> SEQUENCE: 2
gggcgtggct taagggtggg aaagaatata taa                               33
```